(12) United States Patent
Eaton et al.

(10) Patent No.: US 6,875,710 B2
(45) Date of Patent: Apr. 5, 2005

(54) COMPOSITE WEBS WITH REINFORCING POLYMERIC REGIONS AND ELASTIC POLYMERIC REGIONS

(75) Inventors: Bradley W. Eaton, Woodbury, MN (US); Byron M. Jackson, Forest Lake, MN (US); Leigh E. Wood, Woodbury, MN (US); Scott J. Tuman, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 320 days.

(21) Appl. No.: 10/012,698

(22) Filed: Nov. 5, 2001

(65) Prior Publication Data

US 2003/0087098 A1 May 8, 2003

(51) Int. Cl.[7] .................... B32B 27/04; B32B 27/12; B32B 3/06; B32B 3/10; B32B 3/28
(52) U.S. Cl. .................... 442/66; 428/134; 428/136; 428/137; 428/100; 428/141; 428/167
(58) Field of Search ................... 442/66; 428/134, 428/136, 137, 141, 100, 167

(56) References Cited

U.S. PATENT DOCUMENTS

| 5,230,851 | A  | 7/1993  | Thomas |
| 5,458,590 | A  | 10/1995 | Schleinz et al. |
| 5,503,076 | A  | 4/1996  | Yeo |
| 5,843,057 | A  | 12/1998 | McCormack |
| 6,638,605 | B1 | 10/2003 | Ankuda, Jr. et al. |
| 2002/0115972 | A1 | 8/2002 | Dabi et al. |
| 2003/0085485 | A1 | 5/2003 | Seidel et al. |
| 2003/0087059 | A1 | 5/2003 | Jackson et al. |
| 2003/0088220 | A1 | 5/2003 | Molander et al. |
| 2003/0088228 | A1 | 5/2003 | Desai et al. |
| 2003/0091807 | A1 | 5/2003 | Desai et al. |
| 2003/0111166 | A1 | 6/2003 | Uitenbroek et al. |

FOREIGN PATENT DOCUMENTS

| EP | 0 189 351 A2 | 7/1986 |
| EP | 0 189 351 B1 | 3/1991 |
| FR | 1117251 | 5/1956 |
| WO | WO 00/07532 | 2/2000 |

*Primary Examiner*—Terrel Morris
*Assistant Examiner*—Lynda Salvatore
(74) *Attorney, Agent, or Firm*—Gary L. Griswold; Kevin W. Raasch; William J. Bond

(57) ABSTRACT

Methods of manufacturing composite webs including a substrate with one or more reinforcing discrete polymeric regions located on or within the composite web are disclosed. Molten nonelastomeric thermoplastic material of the discrete polymeric region is forced against the substrate by a transfer roll. If the substrate is porous, fibrous, etc., a portion of the nonelastomeric thermoplastic composition may infiltrate the substrate and/or encapsulate fibers of the substrate. The composite webs also include elastomeric thermoplastic material in discrete polymeric regions on or within the composite web.

16 Claims, 14 Drawing Sheets

COMPOSITE WEBS WITH REINFORCING POLYMERIC REGIONS AND ELASTIC POLYMERIC REGIONS

FIELD OF THE INVENTION

The present invention relates to composite webs that include reinforcing discrete polymeric regions and elastic discrete polymeric regions.

BACKGROUND

The manufacture of articles formed of webs that require some reinforcement to withstand forces experienced during use are known. In many cases, reinforcement is simply provided over the entire substrate or web. Such approaches can, however, add cost and weight to the web, as well as stiffness over the entire surface of the web—even in those areas that do not require reinforcement. Furthermore, reinforcing layers that are coextensive with the web may also reduce its breathability.

To address some of these issues, smaller pieces of reinforcing materials may be attached to a web or substrate in selected areas that require reinforcement. The handling and attachment of such discrete pieces can, however, be problematic, by potentially reducing throughput, causing waste (where the discrete pieces are not securely attached), requiring precise registration or location on the web, requiring the use of adhesives or other bonding agents, etc. The discrete pieces may also present relatively sharp that may be the source of irritation or discomfort. The irritation or discomfort can be exacerbated because the reinforcing pieces are typically located on the surface of the substrate.

In addition to reinforcing substrates or webs, it may also be desirable to manufacture articles that exhibit elasticity in addition to reinforcing regions. The manufacture of articles that exhibit elasticity, i.e., the ability to at least partially recover their original shape after moderate elongation, may be desired for a number of reasons. For example, elasticity may be useful in connection with fastening systems for items such as garments (e.g., diapers, training pants, gowns, etc.). Elasticity in garments can provide what may be referred to as dynamic fit, i.e., the ability to stretch and recover in response to movement by the wearer.

Elasticity may also be useful in connection with other applications. For example, some fasteners may provide more consistent attachment if the fastener is held in tension that can be supplied by stretching the fastener and relying on the recovery forces to provide the desired tension. In other instances, elasticity may allow for easy adjustment of the size or length of a fastener or other article.

Although elasticity may be beneficial in a variety of different applications, it may raise issues in manufacturing. Many attempts to provide elasticity rely on separate elastic components that are, e.g., glued or sewn to a backing or other nonelastic member to provide the desired elasticity. The manufacture of such composite articles may be problematic in that secure attachment of the elastic components may be difficult to achieve and/or maintain. Further, the cost and difficulty of providing and attaching separate elastic components may be relatively high. The handling and attachment of separate elastic components can reduce throughput, cause additional waste (where the separate components are not securely attached), etc.

In other instances, an entire article may be constructed to provide the desired elasticity. For example, many elastic fastening systems rely on the use of elastic laminate backings in which the elastic materials are provided in the form of a film that is coextensive with the backing. Such an approach may add costs associated with providing a coextensive elastic layer or layers. Further, many elastic materials are not breathable. If the elastic laminate backings are to be used in garments, it may be desirable to perforate the backing to improve its breathability. Such additional processing does, however, add to the cost of producing the elastic laminate backing. Another potential disadvantage of elastic laminate backings is that it may be difficult to provide any variability in the elastic recovery forces generated in different portions of the backing.

SUMMARY OF THE INVENTION

The present invention provides methods of manufacturing composite webs including a substrate with one or more reinforcing discrete polymeric regions located on or within the composite web and one or more discrete elastic polymeric regions located on or within the composite web.

One advantage of the methods of the present invention is the ability to transfer one or more discrete polymeric regions onto a major surface of a substrate, where the thermoplastic material of the discrete polymeric region can be forced against the substrate by a transfer roll. If the substrate is porous, fibrous, etc., pressure may enhance attachment of the discrete polymeric regions to the substrates by forcing a portion of the thermoplastic composition to infiltrate the substrate and/or encapsulate fibers of the substrate.

Another advantage is the ability to control the shape, spacing, and volume of the discrete polymeric regions. This may be particularly advantageous because these parameters (shape, spacing, and volume) can be fixed regardless of the line speed of the system.

Another advantage of the present invention may be found in the composite depressions and their use, which may improve the formation of reinforcing discrete polymeric regions in accordance with the present invention. The composite depressions may, e.g., improve the transfer of relatively large discrete polymeric regions onto the substrates as well as the transfer of discrete polymeric regions that have a varying thickness.

Another advantage of the methods of the present invention is the ability to provide one or more discrete polymeric regions that extend for the length of the substrate (while not being formed over the width of the substrate, i.e., the discrete polymeric regions are not coextensive with the major surface of the substrate).

Another advantage of the methods of the present invention is the ability to provide different thermoplastic compositions across the width of the substrate, such that some discrete polymeric regions may be formed of one thermoplastic composition, while other discrete polymeric regions are formed of a different thermoplastic composition.

Yet another advantage of the methods of the present invention is the ability to provide one or more discrete polymeric regions on both major surfaces of a substrate. The discrete polymeric regions on the opposing major surfaces may be formed with the same or different features as desired.

In one aspect, the present invention provides an elastic article including a substrate with first and second major surfaces; one or more reinforcing discrete polymeric regions attached to the substrate, wherein each reinforcing discrete polymeric region of the one or more reinforcing discrete polymeric regions is formed of a nonelastomeric thermoplastic composition that infiltrates a portion of substrate; and one or more elastic elements attached to the substrate, wherein each elastic element of the one or more elastic elements includes an elastic discrete polymeric region formed of an elastomeric thermoplastic composition that infiltrates a portion of the substrate.

In another aspect, the present invention provides a method for producing a composite web by providing a first substrate having a first major surface and a second major surface, wherein a plurality of discrete elastomeric polymeric regions formed of an elastomeric thermoplastic composition are located on the first major surface of the first substrate, wherein each discrete elastomeric polymeric region of the plurality of discrete elastomeric polymeric regions infiltrates the first major surface of the first substrate. The method further includes providing a second substrate having a first major surface and a second major surface, a plurality of discrete nonelastomeric polymeric regions formed of a nonelastomeric thermoplastic composition located on the first major surface of the second substrate, wherein each discrete nonelastomeric polymeric region of the plurality of discrete nonelastomeric polymeric regions infiltrates the first major surface of the second substrate; and laminating the first substrate to the second substrate.

In another aspect, the present invention provides a method for producing a composite web by providing a substrate with a first major surface and a second major surface; and forming a plurality of discrete elastomeric polymeric regions formed of an elastomeric thermoplastic composition on the first major surface of the substrate, wherein each discrete elastomeric polymeric region of the plurality of discrete elastomeric polymeric regions infiltrates the first major surface of the substrate. The method further includes forming a plurality of discrete nonelastomeric polymeric regions formed of a nonelastomeric thermoplastic composition located on the first major surface or the second major surface of the substrate, wherein each discrete nonelastomeric polymeric region of the plurality of discrete nonelastomeric polymeric regions infiltrates the second substrate.

In another aspect, the present invention provides a composite web that includes a substrate with first and second major surfaces; a plurality of nonelastomeric discrete polymeric regions attached to the substrate, wherein each nonelastomeric discrete polymeric region of the plurality of nonelastomeric discrete polymeric regions is formed of a nonelastomeric thermoplastic composition that infiltrates a portion of substrate; a plurality of elastomeric discrete polymeric regions attached to the substrate, wherein each elastomeric discrete polymeric region of the plurality of elastomeric discrete polymeric regions is formed of an elastomeric thermoplastic composition that infiltrates a portion of the substrate; and one or more lines of separation in the substrate. The one or more lines of separation define boundaries of a plurality of distinct articles in the composite web, and wherein each article of the plurality of articles includes at least one nonelastomeric discrete polymeric region of the plurality of nonelastomeric discrete polymeric regions and at least one elastomeric discrete polymeric region of the plurality of elastomeric discrete polymeric regions.

These and other features and advantages of methods according to the present invention are described below in connection with various illustrative embodiments of the invention.

DETAILED DESCRIPTION OF ILLUSTRATIVE EMBODIMENTS OF THE INVENTION

As discussed above, the present invention provides methods and systems for producing composite webs that include a substrate with reinforcing discrete polymeric regions located on the surface or within the composite web. Various different constructions will now be described to illustrate various embodiments of the composite webs that can be manufactured in accordance with the methods of the present invention. These illustrative constructions should not be considered to limit the methods of the present invention, which is to be limited only by the claims that follow.

Figure 1:
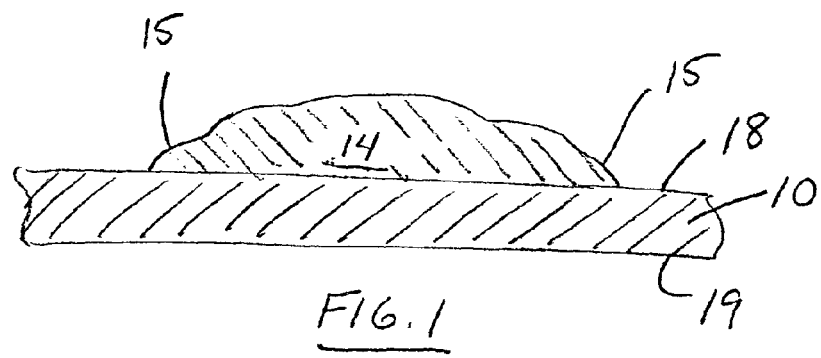
FIG. 1 is a cross-sectional view of one reinforcing discrete polymeric region on a composite web manufactured according to the methods of the present invention.

FIG. 1 is a cross-sectional view of a portion of one composite web manufactured in accordance with the present invention. The composite web includes a substrate 10 with a first major surface 18 and a second major surface 19. One or more reinforcing discrete polymeric regions 14 are located on the first major surface 18 of the substrate 10, it being understood that the substrate may include more than one reinforcing discrete polymeric region as depicted in, e.g., FIGS. 7–12.

It may be preferred that the reinforcing discrete polymeric regions 14 of composite webs manufactured in accordance with the present invention each include a varying thickness or height above the surface 18 of the substrate 10. It may be particularly preferred that the thickness variations be provided in the form of a thinner discrete polymeric region proximate the edges 15 of the reinforcing discrete polymeric region 14.

The combination of thicker central portions of the reinforcing discrete polymeric region 14 and thinner edges 15 may provide advantages. The thinner edges 15 may be more flexible or softer, which may enhance comfort if the composite web including such discrete polymeric regions is incorporated into a garment such as, e.g., a diaper, surgical gown, etc. At the same time, the thicker central portion of the reinforcing discrete polymeric region 14 may provide a desired level of rigidity to the discrete polymeric region.

The reinforcing discrete polymeric regions 14 may cover any desired portion of the surface 18 of the substrate 10 on which they are positioned, although it will be understood that the discrete polymeric regions 14 will not cover all of the surface of the substrate 10. Some variations in the percentage of surface area occupied by discrete polymeric regions may be as described in, for example, pending U.S. patent application Ser. No. 09/257,447, entitled WEB HAVING DISCRETE STEM REGIONS, filed on Feb. 25, 1999 (published as International Publication No. WO 00/50229).

Further, although the discrete polymeric regions 14 are depicted as being disconnected from each other, it should be understood that some composite webs manufactured with the systems and methods of the present invention may include a relatively thin skin layer of the thermoplastic composition used to form the discrete polymeric regions. Such a skin layer may, in some instances, connect some or all of the discrete polymeric regions on the composite web. In any event, however, the amount of polymeric material in the skin layer will be insufficient to provide significant reinforcement of the substrate outside of the thicker discrete polymeric regions. If the composite web includes elastomeric discrete polymeric regions as discussed in connection with FIGS. 18–26, the amount of elastomeric polymeric material in any elastomeric skin layer will be insufficient to provide significant elasticity to the substrate outside of the thicker elastomeric discrete polymeric regions.

The substrates used in connection with the composite webs of the present invention may have a variety of constructions. For example, the substrates may be a woven material, nonwoven material, knit material, paper, film, or any other continuous media that can be fed through a nip point. The substrates may have a wide variety of properties, such as extensibility, elasticity, flexibility, conformability, breathability, porosity, stiffness, etc. Further, the substrates may include pleats, corrugations or other deformations from a flat planar sheet configuration.

In some instances, the substrates may exhibit some level of extensibility and also, in some instances, elasticity. Extensible webs that may be preferred may have an initial yield tensile force of at least about 50 gm/cm, preferably at least about 100 gm/cm. Further, the extensible webs may preferably be extensible nonwoven webs.

Suitable processes for making a nonwoven web that may be used in connection with the present invention include, but are not limited to, airlaying, spunbond, spunlace, bonded melt blown webs and bonded carded web formation processes. Spunbond nonwoven webs are made by extruding a molten thermoplastic, as filaments from a series of fine die orifices in a spinneret. The diameter of the extruded filaments is rapidly reduced under tension by, for example, by non-eductive or eductive fluid-drawing or other known spunbond mechanisms, such as described in U.S. Pat. No. 4,340,563 (Appel et al.); U.S. Pat. No. 3,692,618 (Dorschner et al.); U.S. Pat. Nos. 3,338,992 and 3,341,394 (Kinney); U.S. Pat. No. 3,276,944 (Levy); U.S. Pat. No. 3,502,538 (Peterson); U.S. Pat. No. 3,502,763 (Hartman) and U.S. Pat. No. 3,542,615 (Dobo et al.). The spunbond web is preferably bonded (point or continuous bonding).

The nonwoven web layer may also be made from bonded carded webs. Carded webs are made from separated staple fibers, which fibers are sent through a combing or carding unit which separates and aligns the staple fibers in the machine direction so as to form a generally machine direction-oriented fibrous nonwoven web. However, randomizers can be used to reduce this machine direction orientation.

Once the carded web has been formed, it is then bonded by one or more of several bonding methods to give it suitable tensile properties. One bonding method is powder bonding wherein a powdered adhesive is distributed through the web and then activated, usually by heating the web and adhesive with hot air. Another bonding method is pattern bonding wherein heated calender rolls or ultrasonic bonding equipment are used to bond the fibers together, usually in a localized bond pattern though the web can be bonded across its entire surface if so desired. Generally, the more the fibers of a web are bonded together, the greater the nonwoven web tensile properties.

Airlaying is another process by which fibrous nonwoven webs useful in the present invention can be made. In the airlaying process, bundles of small fibers usually having lengths ranging between about 6 to about 19 millimeters are separated and entrained in an air supply and then deposited onto a forming screen, often with the assistance of a vacuum supply. The randomly deposited fibers are then bonded to one another using, for example, hot air or a spray adhesive.

Meltblown nonwoven webs may be formed by extrusion of thermoplastic polymers from multiple die orifices, which polymer melt streams are immediately attenuated by hot high velocity air or steam along two faces of the die immediately at the location where the polymer exits from the die orifices. The resulting fibers are entangled into a coherent web in the resulting turbulent airstream prior to collection on a collecting surface. Generally, to provide sufficient integrity and strength for the present invention, meltblown webs must be further bonded such as by through air bonding, heat or ultrasonic bonding as described above.

A web can be made extensible by skip slitting as is disclosed in, e.g., International Publication No. WO 96/10481 (Abuto et al.). If an elastic, extensible web is desired, the slits are discontinuous and are generally cut on the web prior to the web being attached to any elastic component. Although more difficult, it is also possible to create slits in the nonelastic web layer after the nonelastic web is laminated to the elastic web. At least a portion of the slits in the nonelastic web should be generally perpendicular (or have a substantial perpendicular vector) to the intended direction of extensibility or elasticity (the at least first direction) of the elastic web layer. By generally perpendicular it is meant that the angle between the longitudinal axis of the chosen slit or slits and the direction of extensibility is between 60 and 120 degrees. A sufficient number of the described slits are generally perpendicular such that the overall laminate is elastic. The provision of slits in two directions is advantageous when the elastic laminate is intended to be elastic in at least two different directions.

A nonwoven web used in connection with the present invention can also be a necked or reversibly necked nonwoven web as described in U.S. Pat. Nos. 4,965,122; 4,981,747; 5,114,781; 5,116,662; and 5,226,992 (all to Morman). In these embodiments the nonwoven web is elongated in a direction perpendicular to the desired direction of extensibility. When the nonwoven web is set in this elongated condition, it will have stretch and recovery properties in the direction of extensibility.

The substrates used in connection with the present invention may preferably exhibit some porosity on one or both of the major surfaces of the substrate such that when a molten thermoplastic composition is provided on one of the major surfaces of the substrate, a mechanical bond is formed between the molten thermoplastic composition and the substrate as the molten thermoplastic composition infiltrates and/or encapsulates a portion of the porous surface of the substrate. As used in connection with the present invention, the term "porous" includes both structures that include voids formed therein, as well as structures formed of a collection of fibers (e.g., woven, nonwoven, knit, etc.) that allow for the infiltration of molten thermoplastic composition into the interstices between fibers. If the porous surface includes fibers, the thermoplastic composition may preferably encapsulate fibers or portions of fibers on the surface of the substrate.

The type and construction of the material or materials in the substrate should be considered when selecting an appropriate substrate to which a molten thermoplastic composition is applied. Generally, such materials are of the type and construction that do not melt, soften, or otherwise disintegrate under the temperatures and pressures experienced during the step of transferring the thermoplastic composition to the substrate. For example, the substrate should have sufficient internal strength such that it does not fall apart during the process. Preferably, the substrate has sufficient strength in the machine direction at the temperature of the transfer roll to remove it intact from the transfer roll.

As used herein, the term "fiber" includes fibers of indefinite length (e.g., filaments) and fibers of discrete length, e.g., staple fibers. The fibers used in connection with the present invention may be multicomponent fibers. The term "multicomponent fiber" refers to a fiber having at least two distinct longitudinally coextensive structured polymer domains in the fiber cross-section, as opposed to blends where the domains tend to be dispersed, random, or unstructured. The distinct domains may thus be formed of polymers from different polymer classes (e.g., nylon and polypropylene) or be formed of polymers from the same polymer class (e.g., nylon) but which differ in their properties or characteristics. The term "multicomponent fiber" is thus intended to include, but is not limited to, concentric and eccentric sheath-core fiber structures, symmetric and asymmetric side-by-side fiber structures, island-in-sea fiber structures, pie wedge fiber structures, and hollow fibers of these configurations.

Although the substrates depicted in the various cross-sectional views of the articles manufactured according to the methods of the present invention are illustrated as single layer structures, it should be understood that the substrates may be of single or multi-layer construction. If a multi-layer construction is used, it will be understood that the various layers may have the same or different properties, constructions, etc. Some of these variations may be as described in, for example, pending U.S. patent application Ser. No. 09/257,447, entitled WEB HAVING DISCRETE STEM REGIONS, filed on Feb. 25, 1999 (published as International Publication No. WO 00/50229).

The discrete polymeric regions 14 may be formed of a wide variety of different nonelastomeric thermoplastic polymeric materials. As used in connection with the present invention, "thermoplastic" (and variations thereof) means a polymer or polymeric composition that softens when exposed to heat and returns to its original condition or near its original condition when cooled to room temperature. The thermoplastic compositions used in connection with the methods of the present invention should be capable of flowing or entering into depressions formed in a polymer transfer roll as will be described below.

Suitable thermoplastic compositions are those that are melt processable. Such polymers are those that will flow sufficiently to at least partially fill the depressions, yet not significantly degrade during a melt process. A wide variety of thermoplastic compositions have suitable melt and flow characteristics for use in the process of the present invention depending on the geometry of the depressions and the processing conditions. It may further be preferred that the melt processable materials and conditions of processing are selected such that any viscoelastic recovery properties of the thermoplastic compositions do not cause them to significantly withdraw from the wall(s) of the depressions until transfer of the thermoplastic composition to a substrate is desired.

Some examples of nonelastomeric thermoplastic compositions that may be used in connection with the present invention include, but are not limited to, polyurethanes, polyolefins (e.g., polypropylenes, polyethylenes, etc.), polystyrenes, polycarbonates, polyesters, polymethacrylates, ethylene vinyl acetate copolymers, ethylene vinyl alcohol copolymers, polyvinylchlorides, acrylate modified ethylene vinyl acetate polymers, ethylene acrylic acid copolymers, nylons, fluorocarbons, etc.

A nonelastomeric thermoplastic polymer is one that melts and returns to its original condition or near its original condition upon cooling and which does not exhibit elastomeric properties at ambient conditions (e.g., room temperature and pressure). As used in connection with the present invention, "nonelastomeric" means that the material will not substantially resume its original shape after being stretched. Further, the nonelastomeric materials may preferably sustain permanent set following deformation and relaxation, which set is preferably at least about 20 percent or more, and more preferably at least about 30 percent or more of the original length at moderate elongation, e.g., about 50% (for those materials that can even be stretched up to 50% without fracture or other failure).

The nonelastomeric thermoplastic compositions used in connection with the present invention can also be combined with various additives for desired effect. These include, for example, fillers, viscosity reducing agents, plasticizers, tackifiers, colorants (e.g., dyes or pigments), antioxidants, antistatic agents, bonding aids, antiblocking agents, slip agents, stabilizers (e.g., thermal and ultraviolet), foaming agents, microspheres, glass bubbles, reinforcing fibers (e.g., microfibers), internal release agents, thermally conductive particles, electrically conductive particles, and the like. The amounts of such materials that can be useful in the thermoplastic compositions can be readily determined by those skilled in the art of processing and using such materials.

Figure 2:
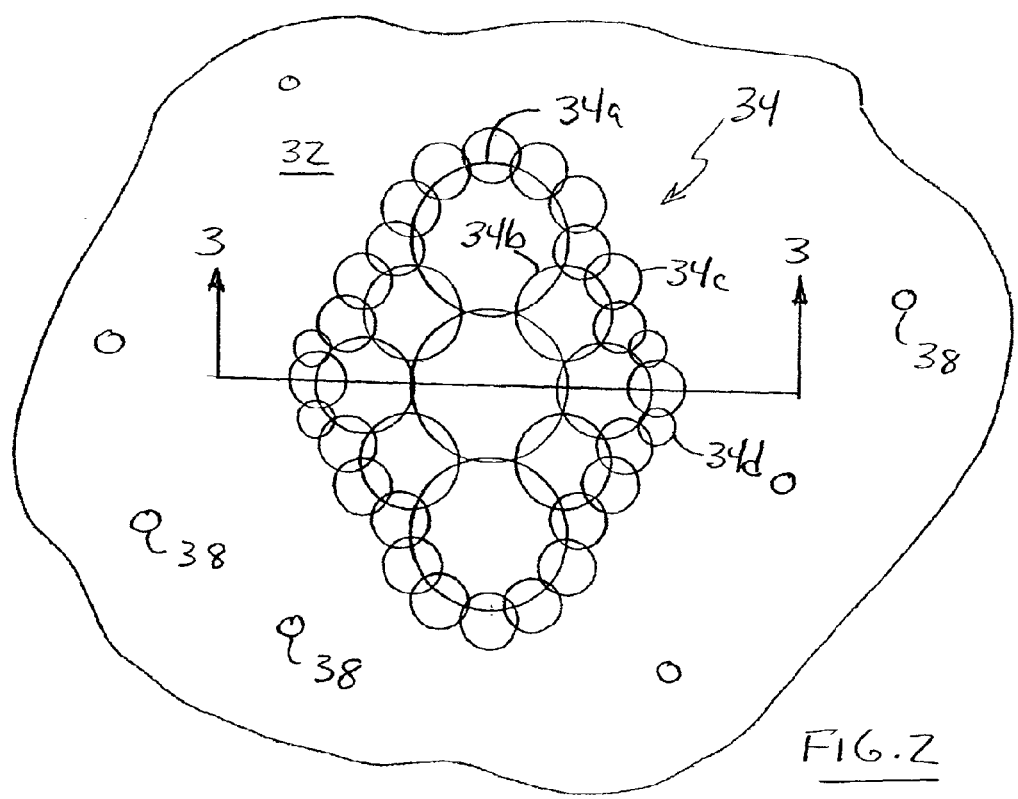
FIG. 2 is a plan view of a portion of a transfer roll that can be used in manufacturing composite webs according to the methods of the present invention.

FIG. 2 is a plan view of a portion of the exterior surface of one transfer tool that can be used to deposit the reinforcing discrete polymeric region 14 on the substrate 10 depicted in FIG. 1. That depicted portion of the exterior surface 32 includes a depression 34 formed therein. FIG. 2 also depicts a number of smaller depressions 38 dispersed over the surface 32 of the transfer roll. Each of the depressions 38 is smaller than the larger depression 34, both in terms of footprint (see below) as well as depression volume. The smaller depressions 38 may also fill with molten thermoplastic composition during use of the transfer roll, with the smaller discrete polymeric regions formed by the depressions 38 serving a variety of purposes as discussed in connection with FIGS. 7–9 below.

Figure 3A:
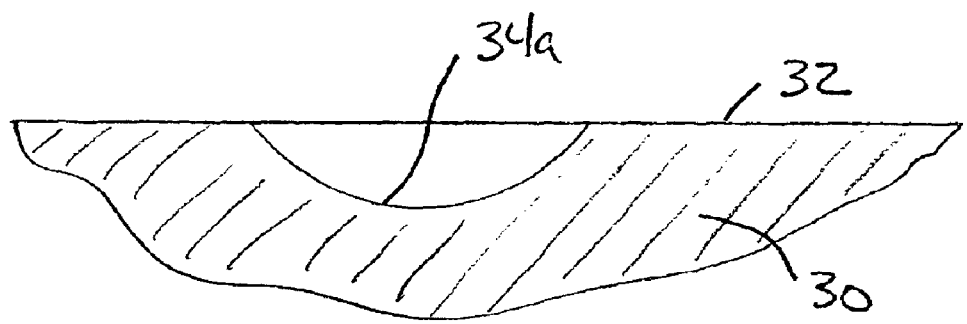
FIG. 3A is a cross-sectional view of the depression of FIG. 2, taken along line 3—3 in FIG. 2 at one point during formation of the depression.
Figure 3B:
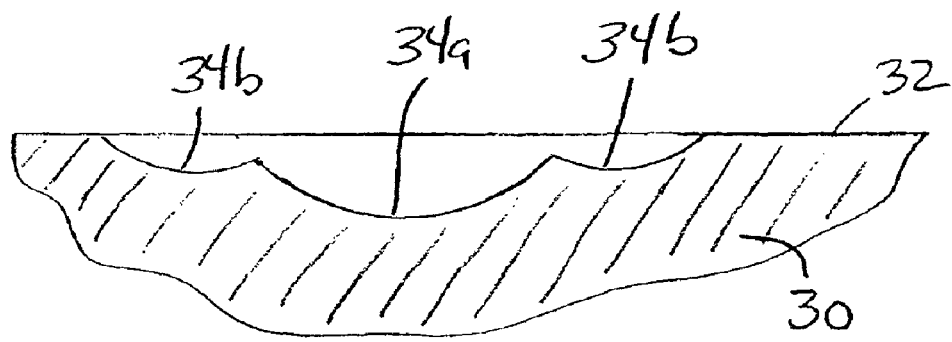
FIG. 3B is a cross-sectional view of the depression of FIG. 2, taken along line 3—3 in FIG. 2 at another point during formation of the depression.
Figure 3C:
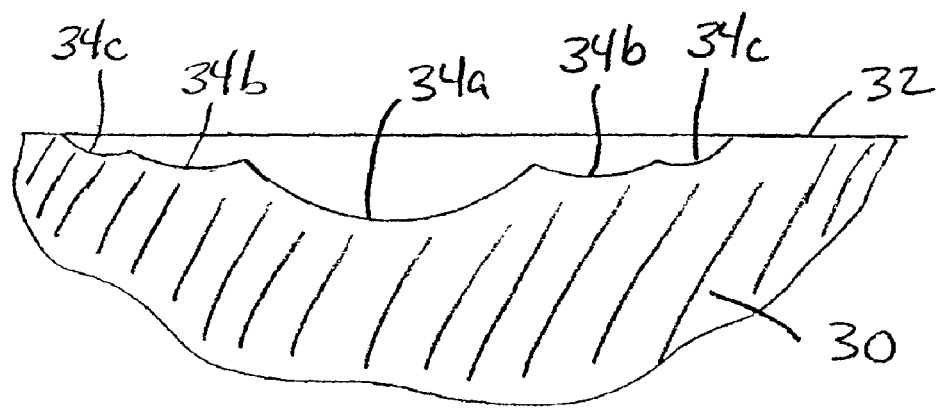
FIG. 3C is a cross-sectional view of the depression of FIG. 2, taken along line 3—3 in FIG. 2 during formation of the depression.

The depression 34 is preferably a composite of cells 34a, 34b, 34c and 34d formed in the surface 32 by any suitable technique, e.g., machining, etching, laser ablation, etc. FIGS. 3A–3C depict one set of steps that can be used to manufacture a composite depression 34 in the transfer roll 30 as seen in FIG. 2. The views in FIGS. 3A–3C are taken along line 3—3 in FIG. 2 and, as a result, do not include the smallest cells 34d seen in FIG. 2.

Further, the complete outline of each of the cells is depicted in FIG. 2 for a better understanding of the invention, although it will be understood that portions of each of the cells may not actually be visible in the finished composite depression 34. In addition, the depicted composite depression 34 is made of a multiple circular cells 34a–34d. It should, however, be understood that composite depressions according to the present invention may be made of cells having any selected shape, e.g., oval, square, triangular, etc. Further, the composite depressions of the present invention may be constructed of cells having a variety of shapes and/or sizes.

In the depicted composite depression 34, cells 34a have the largest diameter and are formed to the greatest depth into the surface 32. Further, the cells 34a may be formed first as seen in FIG. 3A. Alternatively, the smaller cells may be formed first, with the larger cells formed later. The cells 34b may be formed next as depicted in FIG. 3B. Cells 34b are, in the depicted embodiment, formed to a shallower depth in the transfer roll 30 than cell 34a. It can be seen there that the cells 34b overlap the larger cell 34a, such that not all of the outline of the smaller cells 34b is actually formed into the transfer roll 30.

The final step depicted in FIG. 3C is the formation of smaller cells 34c farther outward from the central cell 34a than cells 34b. In the depicted embodiment, these outer cells 34c are formed to a shallower depth than cells 34b, thereby contributing to the general thinning at the edges of a reinforcing discrete polymeric region as seen in, e.g., FIG. 1.

Although not wishing to be bound by any theory, it is hypothesized that the features (e.g., edges, ridges, etc.) formed at the boundaries between the various cells in the composite structure of depression 34 may enhance its ability to retain molten thermoplastic composition during the transfer process as discussed below.

The depressions on transfer rolls used in connection with the present invention may be characterized in terms of the area occupied by their footprint on the exterior surface of the forming tool, a maximum dimension of the footprint (in any direction on the surface of the roll), the volume of the depression, the shape of the footprint, etc.

When characterized in terms of the area occupied by the footprint of the depressions, each of the depressions 34 may have a footprint with an area of about 4 square millimeters ($mm^2$) or more. In other situations, each of the depressions 34 may have footprints with an area of about 8 $mm^2$ or more.

Another manner in which the depressions may be characterized is in terms of the largest footprint dimension as measured on the surface 32 of the transfer roll 30. When characterized in terms of the largest footprint dimension of the footprint, it may be that the depressions have a largest footprint dimension of about 2 mm or more, in some instances about 5 mm or more.

Yet another manner in which the depressions used in connection with the present invention may be characterized is in terms of depression volume. For example, the depressions may have a depression volume of at least about three (3) cubic millimeters ($mm^3$) or more, or alternatively a depression volume of about five (5) cubic millimeters or more. Volume may be important because at least some of the molten thermoplastic composition may be retained within the depression during the transfer process, i.e., the depression volume may preferably be oversized relative to the preferred volume of the discrete polymeric regions to be formed by the depressions to compensate for retention of thermoplastic composition within the depressions.

The orientation of the depression 34 on a transfer roll 30 may be selected based on a variety of factors. The elongated depression 34 may be aligned in the machine direction (i.e., the direction of travel of a substrate), in the cross-web direction (i.e., transverse to the direction of travel of the substrate), or any other orientation between machine direction or cross-web direction.

Figure 4:
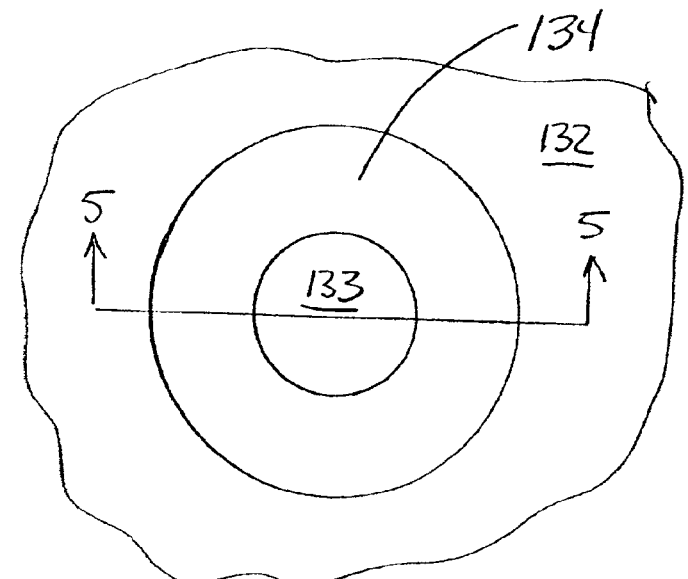
FIG. 4 is a plan view of another depression on a portion of a transfer roll that can be used to manufacture reinforcing discrete polymeric regions on a composite web according to the methods of the present invention.
Figure 5:
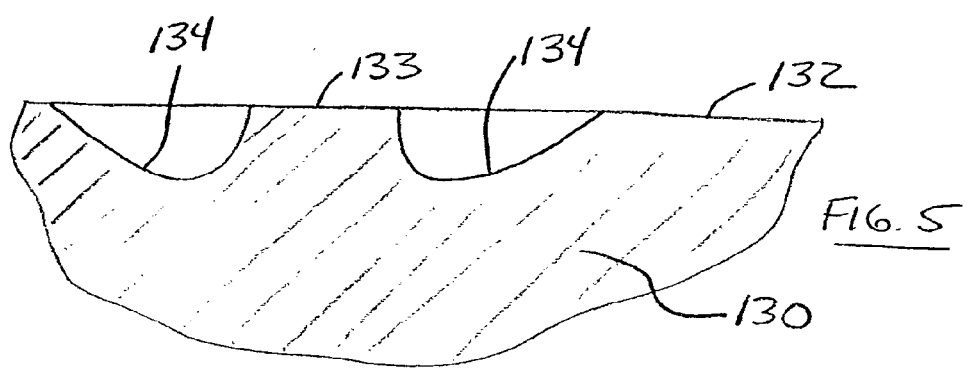
FIG. 5 is a cross-sectional view of the depression of FIG. 4, taken along line 5—5 in FIG. 4.

FIGS. 4 and 5 depict yet another variation in the shape of depressions formed in transfer tools used to provide reinforcing discrete polymeric regions on substrates in connection with the methods of the present invention. The depression 134 is located in the surface 132 of a transfer tool in the shape of a circular trough with an island 133 located in the center of depression 134 formed in the exterior surface 132.

Depressions that include islands such as that depicted in FIG. 4 can be used to provide reinforcing discrete polymeric regions on a substrate in which a portion of the substrate is exposed within a surrounding ring of polymer. The resulting construction may, for example, be used to reinforce the substrate in the area of, e.g., a buttonhole, slot, perforation, or other opening formed on in the substrate. Other uses for similar structures may also be envisioned.

The island 133 formed in the center of depression 134 is preferably the same height as the exterior surface 132 of the transfer roll that surrounds the depression 134. Although the depression 134 is depicted with only a single island 133 formed therein, depressions used in connection with the methods of the present invention may include two or more islands located within each depression if so desired. Furthermore, the shape of the island and surrounding depression may also vary, e.g., a depression that has a circular outermost perimeter may be paired with an island having a different shape. In another variation, the island may not be centered within the depression as depicted in FIG. 4.

Another variation depicted in FIG. 5 is the variation in depth of the depression 134, with the depression being deepest proximate the island and rising to a shallower depth at the outermost perimeter of the depression 134. Such a construction may provide a reinforcing discrete polymeric region with more flexible edges due to thinning of the polymeric region as discussed above in connection with FIG. 1. Further, although the depression 134 is not depicted as having a composite construction as does depression 34 in FIG. 2, the depression 134 including island 133 may advantageously be formed as a composite depression of multiple cells.

Figure 6:
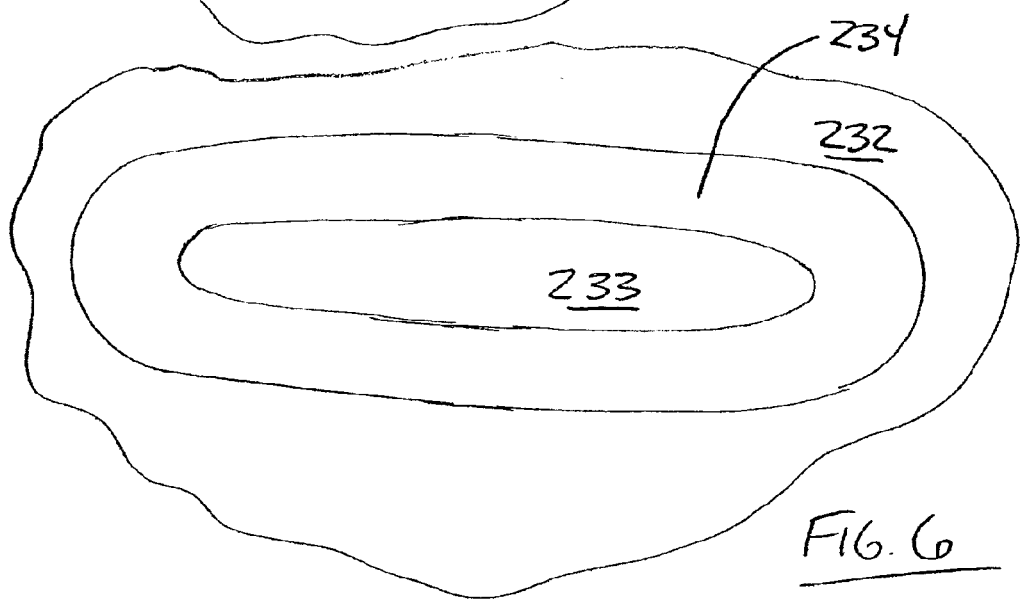
FIG. 6 is a plan view of another depression on a portion of a transfer roll that can be used to manufacture reinforcing discrete polymeric regions on a composite web according to the methods of the present invention.

FIG. 6 depicts another depression 234 formed in the surface 232 of a transfer tool, with the depression 234 also including an island 233 in a manner similar to the depression 134 of FIGS. 4 and 5. Unlike depression 134, the depression 234 is elongated in a generally oval shape that may be more conducive to the formation of a buttonhole or similar structure. Again, although the depression 234 is not depicted as having a composite construction as does depression 34 in FIG. 2, it may advantageously be formed as a composite depression of multiple cells.

Figure 7:
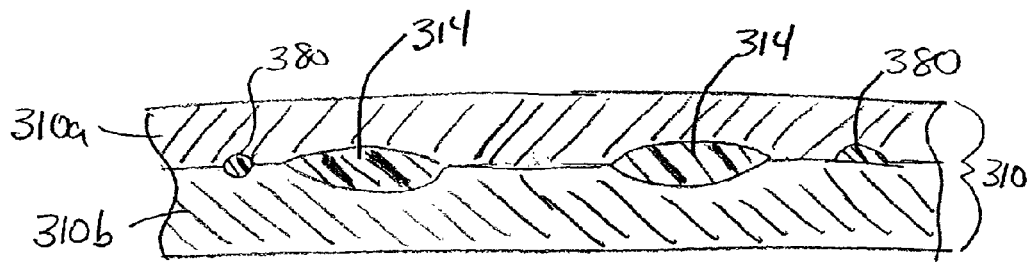
FIG. 7 is a cross-sectional view of a composite web manufactured according to the methods of the present invention including reinforcing discrete polymeric regions between two substrates.
Figure 8:
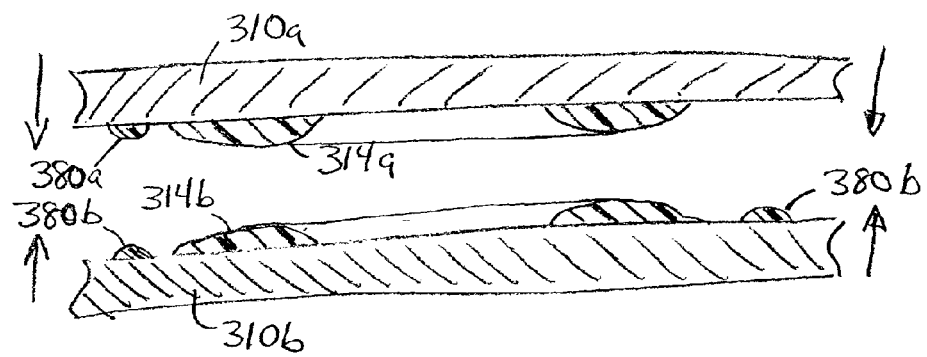
FIG. 8 is a cross-sectional view of the composite web of FIG. 7, before attachment of the two substrates to form the composite web in accordance with the methods of the present invention.

FIGS. 7 and 8 depict yet another variation in a composite web manufactured according to the methods of the present invention. The composite web of FIG. 7 is a laminated structure including a first substrate 310a laminated to a second substrate 310b to form a laminated substrate 310. A number of discrete polymeric regions 314 are located between the two substrates 310a and 310b. A number of smaller discrete polymeric regions 380 are depicted as being located between the larger discrete polymeric regions 314. The smaller discrete polymeric regions 380 are optional, i.e., they may not be required in addition to the larger discrete polymeric regions 314. These smaller features may be helpful to attach the two substrates 310a and 310b together between the larger discrete polymeric regions 314.

In some instances, attachment of the two substrates 310a and 310b may be accomplished using the discrete polymeric regions 314 and 380 alone when the lamination is performed while the polymer regions 314 and 380 are still in a somewhat molten state such that they can bond with counterpart discrete polymeric regions on the opposing substrate or to the opposing substrate itself. One advantage of this construction is that the lamination may be accomplished without the need for additional materials and/or process steps. The lamination between substrates 310a and 310b may alternatively be assisted by a variety of materials and/or techniques known to those skilled in the art, e.g., thermal bonding, adhesives, resins, tie films/webs, etc. See, e.g., U.S. Pat. No. 2,787,244 (Hickin); U.S. Pat. No. 3,694,867 (Stumpf); U.S. Pat. No. 4,906,492 (Groshens); U.S. Pat. No. 5,685,758 (Paul et al.); and U.S. Pat. No. 6,093,665 (Sayovitz et al.).

The laminated construction of FIG. 7 may be useful, for example, to provide a cloth-like or softer feel or appearance, breathability, porosity, etc. on both sides of the composite web. This is in contrast to the composite webs in which the discrete polymeric regions are located on an exposed surface of the composite web. A laminated composite web structure such as that seen in FIG. 7 may also be used to provide different properties on opposite sides of the composite web structure. For example, the porosity or other properties may differ between the different substrates 310a and 310b.

FIG. 8 depicts lamination of the substrates 310a and 310b by forces operating in the directions of the arrows located at both sides of the figure. One of the aspects depicted in FIG. 8 is the combination of discrete polymeric regions 314a on substrate 310a with discrete polymeric regions 314b located on the opposing surface of substrate 310b to form the discrete polymeric regions 314 in the composite web as depicted in FIG. 7.

Another aspect depicted in FIG. 8 is that the smaller polymeric regions 380 seen in FIG. 7 may be constructed from the combination of a polymeric region 380a on substrate 310a and a polymeric region 380b on substrate 310b. In other instances, the smaller polymeric region is located on only one of the substrates 310a or 310b and preferably bonds directly to the opposing substrate during lamination. Similarly, in some instances the larger discrete polymeric regions 314 may be formed by depositing polymer on only one of the substrates 310a or 310b before attaching the opposing substrate.

Another potential advantage of the laminated construction of the composite web seen in FIGS. 7 and 8 is that the reinforcing discrete polymeric regions 314 formed by laminating two separate polymeric regions 314a and 314b together may provide a combined reinforcing discrete polymeric region 314 that contains more polymer than could be effectively deposited as a single reinforcing discrete polymeric region using the methods of the present invention. That additional polymer may provide reinforcing discrete polymeric regions that are stiffer, thicker, or have other advantageous features.

Figure 9:
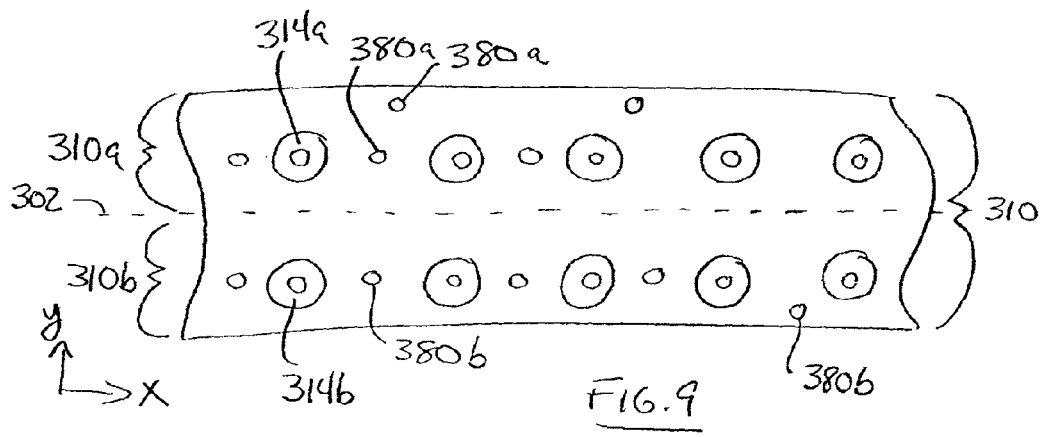
FIG. 9 is a plan view of one illustrative substrate with reinforcing discrete polymeric regions formed thereon that can be manufactured into a composite web according to the methods of the present invention.

FIG. 9 is a plan view of a composite web that may be used to form the composite web depicted in FIG. 7 in which two portions 310a and 310b of a single, unitary substrate 310 can be folded along a fold line 302 to provide the laminated structure of FIGS. 7 and 8. Alternatively, the substrates 310a and 310b as seen in, e.g., FIG. 8, may be separate from each other before lamination. The substrate 310 includes opposing reinforcing discrete polymeric regions 314a and 314b on portions 310a and 310b that are combined when the substrate 310 is folded along fold line 302.

The substrate 310 also includes a number of opposing smaller discrete polymeric regions 380a and 380b on portions 310a and 310b that are combined when the substrate 310 is folded along fold line 302. Further, the substrate 310 includes some smaller discrete polymeric regions 380a and 380b that do not oppose any similar deposits on the opposite side of the fold line 302.

Although the discrete polymeric regions 314a and 314b are shown as being uniformly spaced over the surface of the substrate 310 in a regular, repeating pattern (in both the x and y directions), it should be understood that spacing between the reinforcing discrete polymeric regions 314a and 314b may be non-uniform if so desired. Furthermore, the pattern in which the reinforcing discrete polymeric regions are arranged, may be irregular and/or non-repeating.

In other variations, portions of the composite webs manufactured in accordance with the present invention may include uniformly-spaced discrete polymeric regions as depicted in FIG. 9 while other portions of the same composite web may be free of any discrete polymeric regions. In yet another alternative, portions of the composite web manufactured in accordance with the present invention may include uniformly spaced discrete polymeric regions as seen in FIG. 9, while other portions of the same composite web may include discrete polymeric regions that are arranged in a non-uniform and/or non-repeating patterns. Further, different portions of a composite web manufactured according to the present invention may include different sets of discrete polymeric regions that are both uniformly spaced in repeating patterns that are different from each other.

The discrete polymeric regions could be provided in any desired shape, e.g., squares, rectangles, hexagons, etc. The shapes may or may not be in the form of recognized geometric shapes, but may be randomly formed with irregular perimeters. In addition, the shapes may not necessarily be solid figures, but may include islands formed within the shape in which none of the thermoplastic composition is transferred. In yet another alternative, some or all of the discrete polymeric regions may be in the form of indicia, i.e., letters, numbers, or other graphic symbols.

Figure 10:
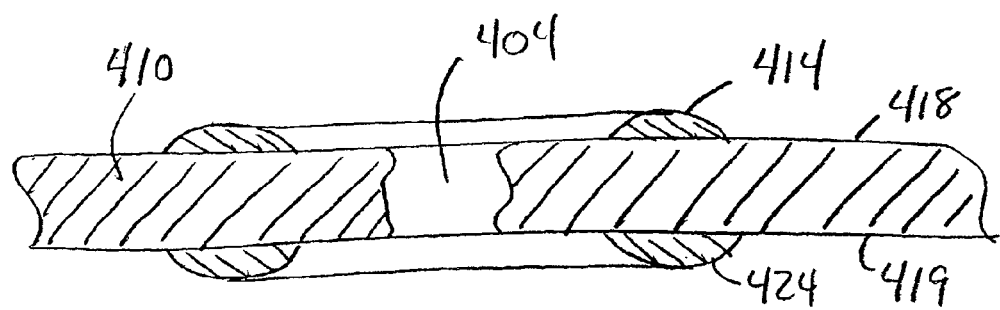
FIG. 10 is a cross-sectional view of another composite web with reinforcing discrete polymeric regions on both major surfaces of a substrate.

FIG. 10 illustrates yet another embodiment of a composite web manufactured in accordance with the present invention. The composite web includes a substrate 410 with opposing major surfaces 418 and 419. One feature illustrated in FIG. 10 is the two-sided nature of the reinforcing discrete polymeric regions located on the opposing major surfaces 418 and 419, respectively. Reinforcing discrete polymeric region 414 is provided on major surface 418 and reinforcing discrete polymeric region 424 is provided on opposing major surface 419. Both discrete polymeric region 414 and discrete polymeric region 424 are exposed on opposite sides of the composite web.

The discrete polymeric regions on opposing major surfaces are depicted as being in registration through the substrate 410. In other words, the discrete polymeric region 414 is aligned with the discrete polymeric region 424 on the opposite side of the substrate 410. Further, the discrete polymeric region 414 is depicted as being substantially the same size as the discrete polymeric region 424 located on the opposite side of the substrate 410. It should, however, be understood that when a composite web having discrete polymeric regions on both major surfaces is desired, the discrete polymeric regions on the opposing surfaces may or may not be the same size as seen in FIG. 10. Also, it should be understood that the discrete polymeric regions may or may not be in registration with each other through the substrate 410 as seen in FIG. 10.

The reinforcing discrete polymeric regions 414 and 424 may be envisioned as forming a grommet structure on the substrate 410. As a result, it may be desired to provide an optional opening 404 through the substrate 410 as seen in FIG. 10. The opening may be formed by any suitable technique, e.g., mechanical perforation with a tool, laser ablation, water or gas-jet cutting, etc. It will be understood that similar openings could be provided in, e.g., the laminated composite web seen in FIG. 7 as well.

Figure 11:
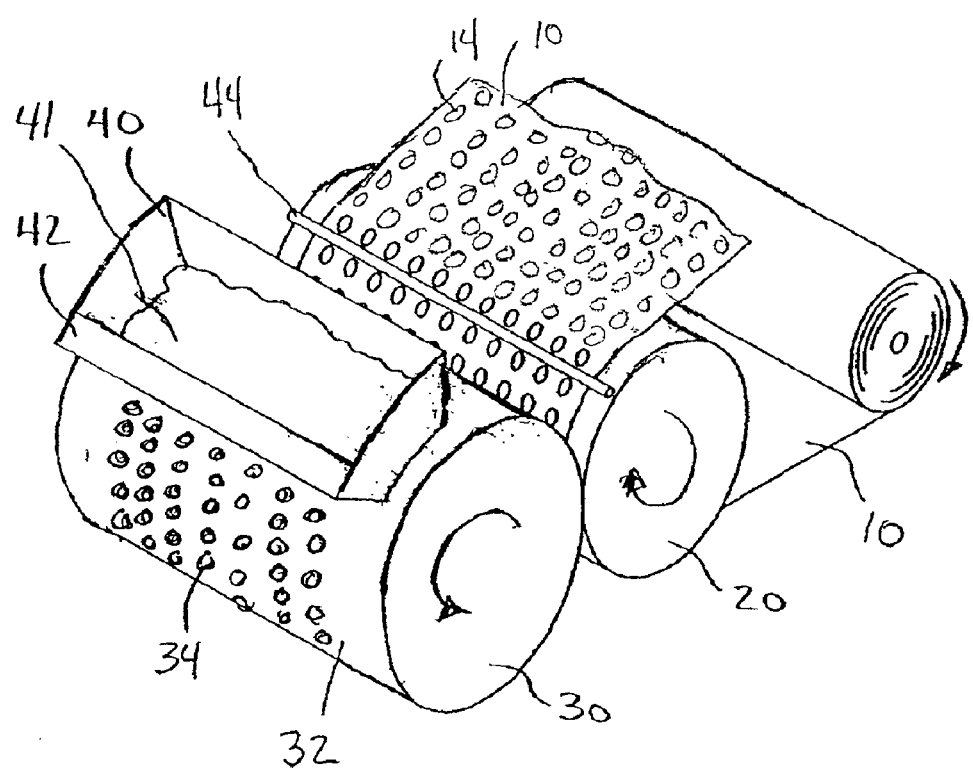
FIG. 11 is a perspective view of one polymer transfer process useful in providing discrete polymeric regions on a substrate in accordance with the methods of the present invention.

FIG. 11 is a perspective view of one system and method of providing discrete polymeric regions on one surface of a substrate 10 in accordance with the principles of the present invention. The system depicted in FIG. 11 includes a substrate 10 that defines a web path through the system. The substrate 10 moves through the system in a downstream direction indicated by the rotation arrows on the various rolls. After being unwound or otherwise provided from a supply (e.g., the substrate 10 may be manufactured in-line with the system depicted in FIG. 11), the substrate 10 is directed into a transfer nip formed between a backup roll 20 and a transfer roll 30.

The process of providing discrete polymeric regions on the substrate 10 includes delivering a supply of a molten thermoplastic composition to the exterior surface 32 of transfer roll 30 that includes a one or more depressions 34 formed in its exterior surface 32. The molten thermoplastic composition 41 is supplied to the exterior surface 32 of the transfer roll 30 by a delivery apparatus in the form of a trough 40 (or other supply apparatus, e.g., extruder, gear pump, etc.).

The excess molten thermoplastic composition is wiped or removed from the exterior surface 32 by a doctor blade 42 acting against the exterior surface 32 of the transfer roll 30. Although it may be ideal to remove all of the thermoplastic composition from the exterior surface 32 of the transfer roll 30, some of the thermoplastic composition may remain on the exterior surface 32 after wiping by the doctor blade 42.

The depressions 34 formed in the exterior surface 32 of the transfer roll 30 preferably receive a portion of the molten thermoplastic composition when the molten thermoplastic composition is deposited on the exterior surface 32 of the transfer roll 30. If the depressions 34 are not completely filled during or by the deposition of molten thermoplastic composition, the wiping action of the doctor blade 42 on the exterior surface 32 of the transfer roll 30 may assist in substantially filling the depressions with molten thermoplastic composition.

Control over the temperatures of the various rolls in the system depicted in FIG. 11 may be useful in obtaining the desired products. It may be preferred, e.g., that the exterior surface 32 of the transfer roll 30 be heated to a selected temperature that is at or above the melt temperature of the thermoplastic composition to be transferred to the substrate 10. Heating the transfer roll 30 may also enhance filling of the depressions 34 by the molten thermoplastic composition.

Because the molten thermoplastic composition 41 is itself heated within the trough 40, the doctor blade 42 will typically be heated by the molten thermoplastic composition. It may alternatively be desirable to control the temperature of the doctor blade 42 separately from the trough 40 containing the molten thermoplastic composition 41. For example, it may be desirable to heat the doctor blade 42 to a temperature above the melt temperature of the molten thermoplastic composition.

Figure 11A:
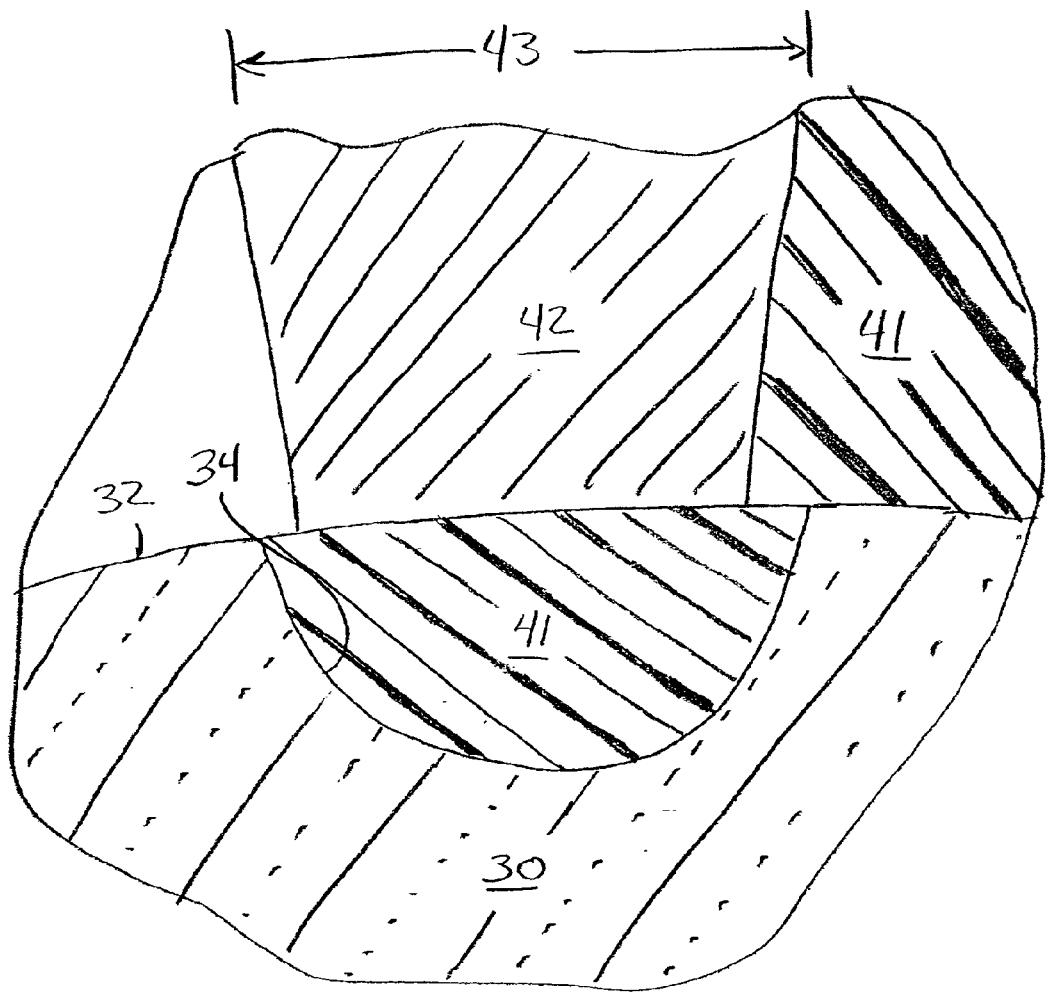
FIG. 11A is an enlarged schematic diagram depicting the relationship between a doctor blade and a depression on a transfer roll used in connection with the present invention.

FIG. 11A is an enlarged partial cross-sectional view depicting one relationship between a doctor blade 42 and depression 34 in a transfer roll 30. Another characteristic of the doctor blade 42 that may be controlled is its thickness or length 43 along the exterior surface of the transfer roll 30 (as measured in the machine direction or the direction of rotation of the transfer roll). For example, a thicker or longer doctor blade 42 may help by allowing the molten thermoplastic composition more time to relax within the depressions 34, thereby improving filling of the depressions. In addition to varying the length of the doctor blade 42, the pressure or force exerted on the transfer roll 30 by the doctor blade 42 may also be adjusted based on a variety of factors including, e.g., the characteristics of the molten thermoplastic composition, the transfer roll characteristics, etc.

With the depressions 34 at least partially filled with the desired molten thermoplastic composition, the transfer roll 30 continues to rotate until the depressions 34 and the molten thermoplastic composition they contain are forced into contact with the substrate 10 against backup roll 20 at the transfer nip (i.e., the nip formed by the transfer roll 30 and the backup roll 20. It is at this point that transfer of the molten thermoplastic composition in the depressions 34 to the substrate 10 begins. It should be understood that under certain conditions, only a portion of the thermoplastic composition in the depressions 34 may transfer to the substrate 10.

When a substrate 10 that includes one or more porous major surfaces on which the molten thermoplastic composition is deposited is used in connection with the methods of the present invention, a mechanical bond is preferably formed by infiltration of the molten thermoplastic composition into the porous surface of the substrate 10. As used in connection with the present invention, the term "porous" includes both structures that include voids formed therein, as well as structures formed of a collection of fibers (e.g., woven, nonwoven or knit) that allow for the penetration of molten thermoplastic compositions.

The nip pressure between the transfer roll 30 and the backup roll 20 is preferably sufficient such that a portion of the thermoplastic composition in the discrete polymeric regions infiltrates and/or encapsulates a portion of the porous substrate 10 to improve attachment of the discrete polymeric regions to the substrate 10. Where the surface of the substrate 10 includes fibers (e.g., where the substrate 10 includes woven, nonwoven, or knit materials on its major surfaces), it may be preferred that the thermoplastic composition encapsulate all or a portion of at least some of the fibers on the surface of the substrate 10 to improve attachment of the discrete polymeric regions to the substrate 10.

Under some conditions the molten thermoplastic composition in the depressions 34 may completely permeate the substrate 10 if, e.g., the substrate 10 is porous throughout its thickness. In other instances, penetration of the molten thermoplastic composition may be limited to the outer layer or layers of the substrate 10.

It should, however, be understood that although the outer surfaces of the substrate 10 may exhibit some porosity, that porosity may not necessarily extend through the entire thickness of the substrate 10. For example, the substrate 10 may have a variety of different layers, with one of the layers being substantially non-porous. In another alternative, the overall thickness of the substrate 10 may render it non-porous as a whole, even though the outer surfaces of the substrate 10 exhibit some porosity as discussed above.

The backup roll 20 may possess a variety of different characteristics depending on the types of substrate materials and/or molten thermoplastic compositions being processed. In some instances, the exterior of the backup roll 20 may be a rubber or other conformable material that conforms to the shape of the transfer roll 30. If a conformable material such as rubber is used, it may, e.g., have a durometer of, e.g., about 10–90 Shore A.

Figure 11B:
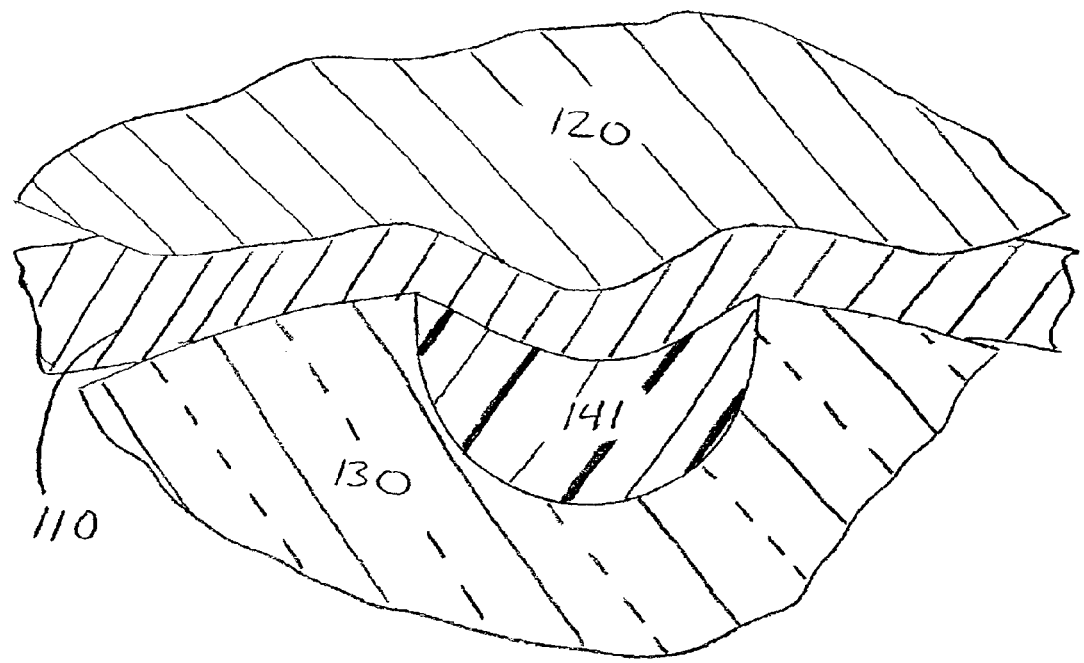
FIG. 11B is an enlarged partial cross-sectional view depicting a conformable backup roll forcing a substrate against a transfer roll.

One such variation at the transfer nip is depicted in FIG. 11B, in which a conformable backup roll 130 is depicted as forcing a portion of the substrate 110 into the depression 134 (and the thermoplastic composition 141 contained therein). If the surface of the substrate 110 facing the depression 134 is porous, a portion of the molten thermoplastic composition 141 may be forced in the porous surface of the substrate 110. Forcing the substrate 110 into the depression may be particularly beneficial if the depression 134 is not completely filled with the molten thermoplastic composition 141 to improve the likelihood of contact between the substrate 10 and the molten thermoplastic composition 141.

Figure 11C:
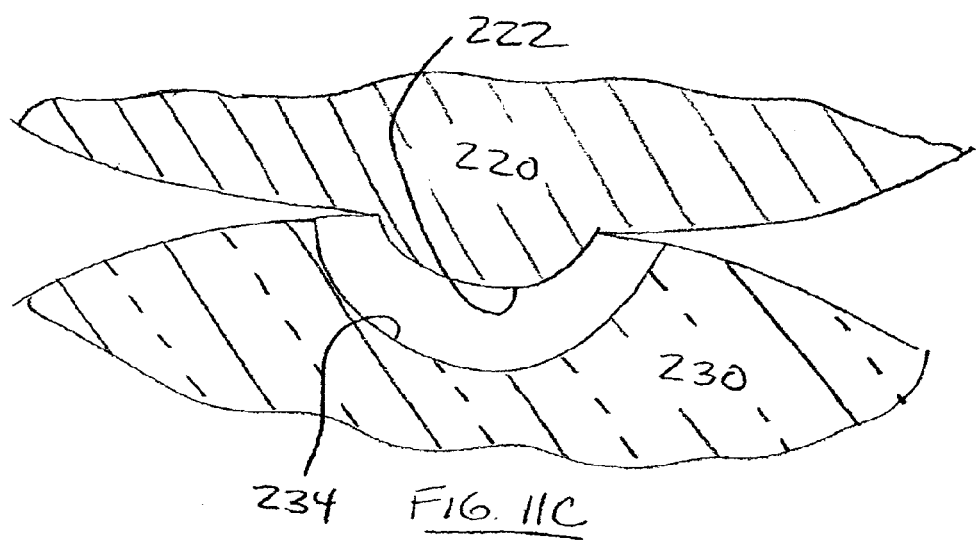
FIG. 11C is an enlarged partial cross-sectional view depicting a mating backup roll including protrusions aligned with depressions in the transfer roll.

Alternatively, the surface of the substrate may be forced into the depressions on the transfer roll using a mating backup roll. This variation at the transfer nip is depicted in FIG. 11C in which the backup roll 220 includes protrusions 222 that are complementary to or mate with the depressions 234 on the transfer roll 230. The protrusions 222 would preferably force a substrate into the depressions with the same results and benefits described above with respect to FIG. 11B. A mating backup roll 220 could be formed of any conformable material, nonconformable material, or combination of conformable or nonconformable materials.

Heating or otherwise controlling the temperature of the transfer roll is discussed above. It should also be appreciated that the temperature of the exterior surface of the backup roll may be controlled. For example, it may be desirable to cool the surface of the backup roll to a selected temperature below the temperature of the transfer roll. Cooling of the backup roll may be beneficial in maintaining the integrity of the substrate, particularly if the substrate integrity can be degraded from the heat of the transfer roll (if the transfer roll is heated) and/or the molten thermoplastic composition in the depressions of the transfer roll.

The substrate 10 continues around the backup roll 20 as seen in FIG. 11. In some instances, a portion of the molten thermoplastic composition in the depressions may remain in the depressions 34 while the substrate 10 is pulled away from the transfer roll 30. As a result, the molten thermoplastic composition in the depressions 34 may tend to elongate or string between the depressions in transfer roll 30 and the substrate 10.

A device, such as a hot wire 44 seen in FIG. 11, may be used to sever any strands of thermoplastic composition that may be formed as the substrate 10 separates from the transfer roll 30. Other devices and/or techniques may be used to accomplish the desired severing of any molten thermoplastic composition strands. Examples may include, but are not limited to hot air knives, lasers, etc. Furthermore, under certain conditions, stringing of the thermoplastic composition may not be encountered during manufacturing.

The tendency of the molten thermoplastic composition in the depressions 34 to string as the substrate exits the transfer nip also raises another issue that should be considered when developing processes according to the present invention. That issue is the internal cohesive strength of the substrate 10 and/or the tensile strength of the substrate 10. This issue may be of more concern if the substrate 10 includes a fibrous construction (e.g., woven, nonwoven, or knit fibers) that could be separated from the remainder of the substrate by the forces exerted when the substrate 10 is pulled away from the transfer roll 30. These considerations may be more important if the molten thermoplastic composition has properties (e.g., tackiness, tensile strength, etc.) such that strands of the molten thermoplastic composition can exert forces on the substrate 10 that exceed the internal cohesive strength and/or tensile strength of the substrate 10.

For example, if the substrate 10 includes a resin-bonded nonwoven portion, the temperature of the transfer roll 30 and/or molten thermoplastic composition may rise above the melting temperature of the resin, thereby potentially degrading the internal cohesive strength and/or tensile strength of the substrate 10. Alternatively, a nonwoven substrate may include fibers that have a melting temperature similar to the temperature of the transfer roll 30 and/or molten thermoplastic composition, thereby potentially degrading the internal cohesive strength and/or tensile strength of the substrate 10.

In either instance, the roll temperatures and/or molten thermoplastic composition temperature may need to be controlled to maintain the integrity of the substrate while transferring the molten thermoplastic composition. For example, the backup roll 20 may be cooled to, in turn, cool the substrate 10 to maintain its internal cohesive strength.

In another alternative, heating of the transfer roll 30 and/or backup roll 20 may be used to enhance the internal cohesive strength and/or tensile strength of the substrate 10. For example, if the substrate 10 includes multi-component fibers or fibers having different compositions, some consolidation of the fibers or other components in the substrate 10 may be caused by heating the substrate 10 while transferring the molten thermoplastic composition from the transfer roll 30 to the substrate 10. That consolidation may improve the integrity of the substrate by forming a skin layer or other strength-enhancing structure on or within the substrate 10. Some exemplary processes may be described in, e.g., U.S. Pat. No. 5,470,424 (Isaac et al.).

Although the system and method depicted in FIG. 11 produces composite webs with reinforcing discrete polymeric regions on only one major side thereof, those of skill in the art will recognize the modifications required to provide discrete polymeric regions on both major surfaces of the substrate in accordance with the principles of the present invention. One example may include, e.g., forming discrete polymeric regions on one surface of each of two separate substrates, with the two substrates then being laminated together to form a single substrate with discrete polymeric regions on both major surfaces (see, e.g., FIG. 10). Alternatively, a single substrate may be directed into a nip formed by two transfer rolls, with each of the transfer rolls depositing discrete polymeric regions on both sides of the web essentially simultaneously.

Figure 12:
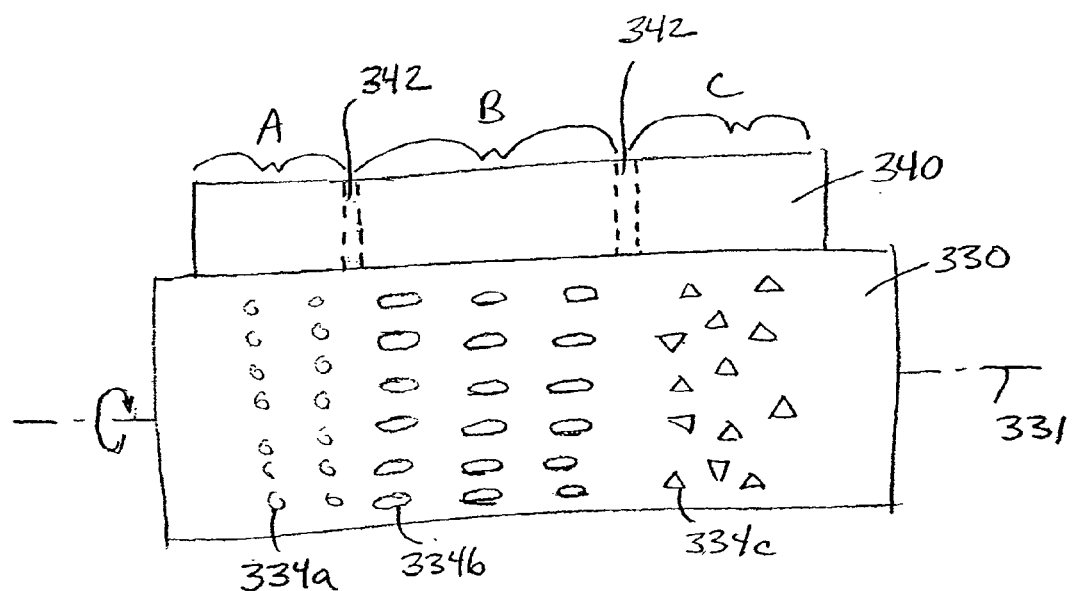
FIG. 12 illustrates another transfer roll and polymer source useful in connection with zoned delivery systems and methods.

Although FIG. 11 depicts the application of only one thermoplastic composition using the transfer roll 30, it will be understood that two or more different thermoplastic compositions may be applied to the exterior surface of the transfer roll 30. FIG. 12 depicts a portion of one system in which a trough 340 is used to deliver three molten thermoplastic compositions (in zones A, B, & C) to the surface of a transfer roll 330 that rotates about an axis 331. The trough 340 may, for example, include barriers 342 such that molten thermoplastic compositions in the different zones of the trough 340 do not mix during processing. In another alternative, separate and distinct troughs could be used for each different thermoplastic composition to be applied to the transfer roll 330.

The transfer roll 330 also includes different sets of depressions 334a, 334b, and 334c over which the different molten thermoplastic compositions may be applied. The depressions in the different zones on transfer roll 330 are differently shaped, have different sizes, and have different spacings. For example, the triangular depressions in zone C are arranged in an irregular, non-repeating pattern while the depressions in zones A & B are arranged in regular, repeating patterns.

With the system of FIG. 12, different sets of discrete polymeric regions may be formed on a single substrate using different thermoplastic compositions. As a result, the thermoplastic compositions may be selected for any of a number of different properties related to manufacturing or end-use performance of the finished articles made using the composite webs.

Figure 13:
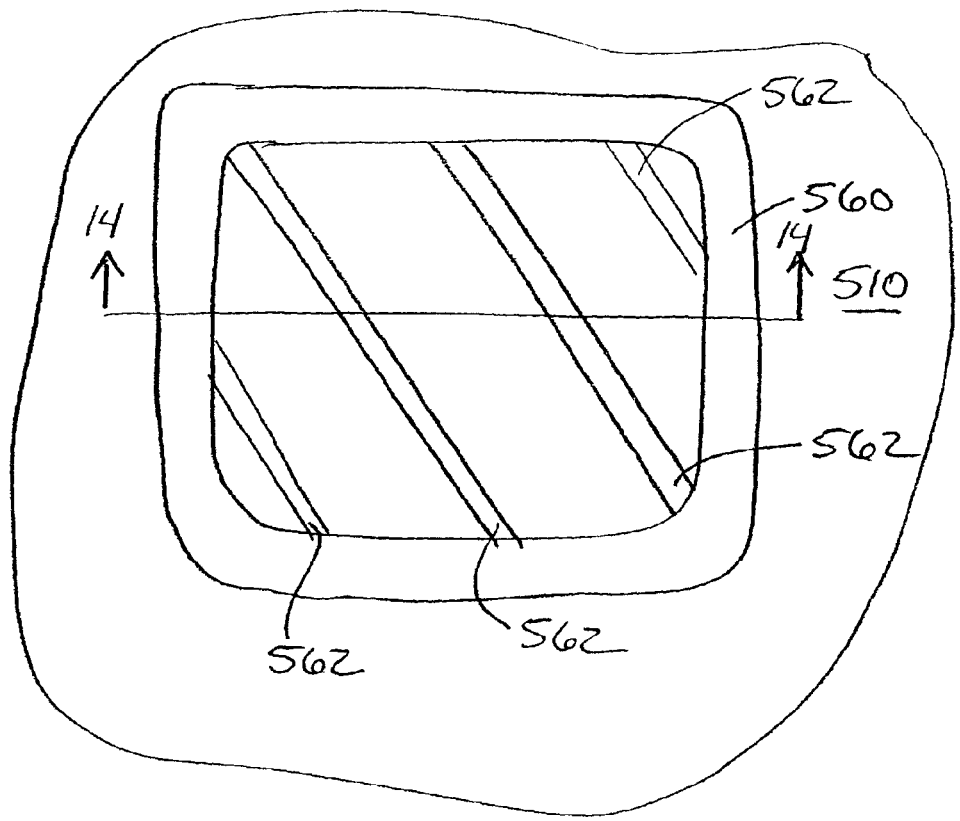
FIG. 13 is a plan view of one article formed in a composite web by providing reinforcing discrete polymeric regions on a substrate according to the methods of the present invention.
Figure 14:
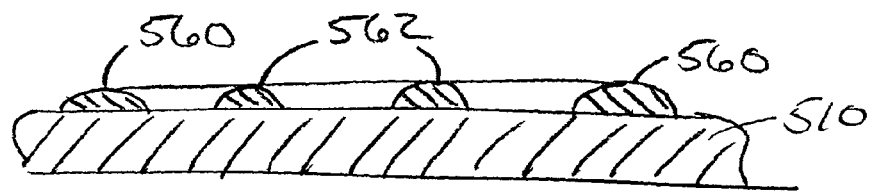
FIG. 14 is a cross-sectional view of the article of FIG. 13 taken along line 14—14 in FIG. 13.

FIGS. 13 and 14 depict an article that may be manufactured from a composite web according to the methods of the present invention, with FIG. 13 being a plan view of the article and FIG. 14 being a cross-sectional view of the article taken along line 14—14 in FIG. 13. The article includes a frame 560 formed by a reinforcing discrete polymeric region on a substrate 510. The article may be, e.g., a filter in which the frame 560 provides an integral support for substrate 510 which functions as filter media. The frame 560, when deposited as a reinforcing discrete polymeric region, preferably does not require the use of bonding agents (e.g., adhesives, etc.) to secure the frame 560 to the filtration substrate 510.

The depicted article also includes one or more optional reinforcement strips 562 that extend across the central area of substrate 510 defined by the frame 560. The reinforcement strips 562 may also preferably be formed by discrete polymeric regions deposited on the substrate 510 according to the methods of the present invention. The reinforcement strips 562 may be formed of the same or different polymeric compositions as the frame 560.

Figure 15:
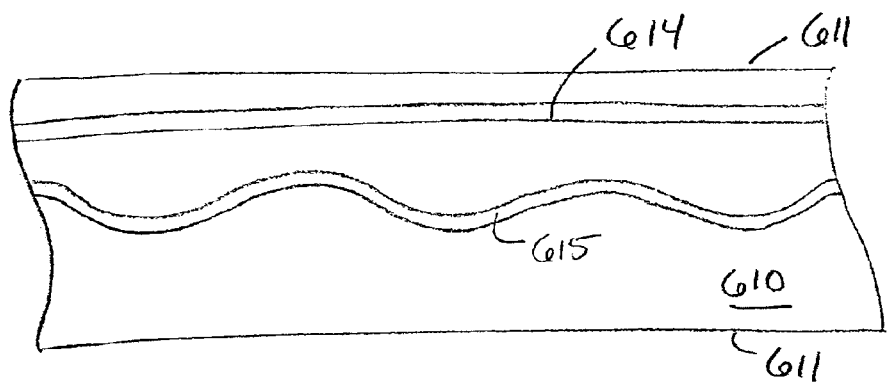
FIG. 15 is a plan view of a portion of one composite web manufactured according to the present invention.
Figure 16:
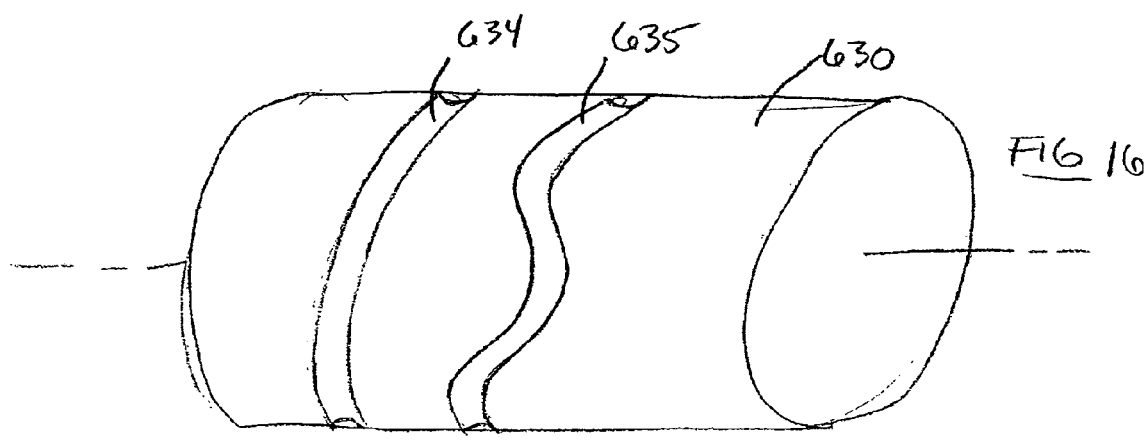
FIG. 16 is a perspective view of one transfer roll that may be used to manufacture the composite web of FIG. 15.

FIGS. 15 & 16 depict another variation associated with the methods of manufacturing composite webs according to the present invention. FIG. 15 depicts, in a plan view, a portion of a composite web manufactured according to the present invention. The composite web includes a substrate 610 on which two discrete polymeric regions 614 and 615 are located. The substrate 610 includes two opposing edges 611 that extend over the length of the composite web and, together, define the longitudinal length of the composite web.

Discrete polymeric region 614 is provided in the shape of a line of the thermoplastic composition material deposited on the substrate 610 along the general direction of the longitudinal length of the composite web. The discrete polymeric region 614 may be continuous along the longitudinal length of the composite web as shown in FIG. 15.

Discrete polymeric region 615 is a variation of discrete polymeric region 614 in that it is provided in an undulating shape as compared to the relative straight linear shape of the discrete polymeric region 614. The undulating shape of the discrete polymeric region 615 also, however, extends along the direction of the longitudinal length of the composite web. Further, the discrete polymeric region 615 may be continuous along the longitudinal length of the composite web as shown in FIG. 15.

FIG. 16 is a perspective view of one transfer roll 630 that may be used to transfer molten thermoplastic compositions to a substrate in the shapes seen in FIG. 15 according to the methods of the present invention. The transfer roll 630 includes a depression 634 that preferably extends continuously around the outer circumference of the transfer roll 630 to form the discrete polymeric region 614 as depicted in FIG. 15. The transfer roll 630 also includes a depression 635 that also extends around the outer circumference of the roll 630 to form the discrete polymeric region 615 as depicted in FIG. 15.

Figure 17:
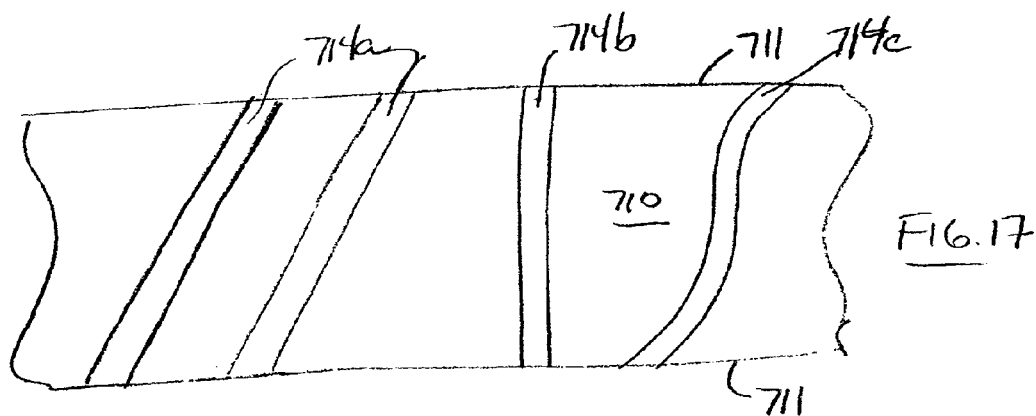
FIG. 17 is a plan view of a portion of one composite web manufactured according to the present invention that includes discrete polymeric regions extending across the width of the substrate.

FIG. 17 depicts another variation associated with the methods of manufacturing composite webs according to the present invention. FIG. 17 depicts, in a plan view, a portion of a composite web manufactured according to the present invention. The composite web includes a substrate 710 on which discrete polymeric regions 714*a*, 714*b*, and 714*c* are located, with the discrete polymeric regions extending across the width of the substrate. The substrate 710 includes two opposing edges 711 that extend over the length of the composite web and, together, define the width and the longitudinal length of the composite web.

Each of the discrete polymeric regions 714*a*, 714*b*, and 714*c* is provided in the shape of a line of the thermoplastic composition material deposited on the substrate 710 in a generally cross-web direction, i.e., extending between the opposing edges 711 of the substrate 710. The discrete polymeric regions 714*a*, 714*b*, and 714*c* present variations from straight lines 714*a* and 714*b* to undulating line 714*c*. Many other variations in placement, shape and/or orientation of reinforcing discrete polymeric regions may be envisioned in connection with methods according to the present invention.

In addition to the provision of articles that include discrete polymeric regions of nonelastomeric thermoplastic compositions on or within a composite web, it may also be desirable to provide such reinforced composite webs with one or more discrete polymeric regions of elastomeric thermoplastic compositions to provide elasticity to the resulting composite webs.

Figure 18:
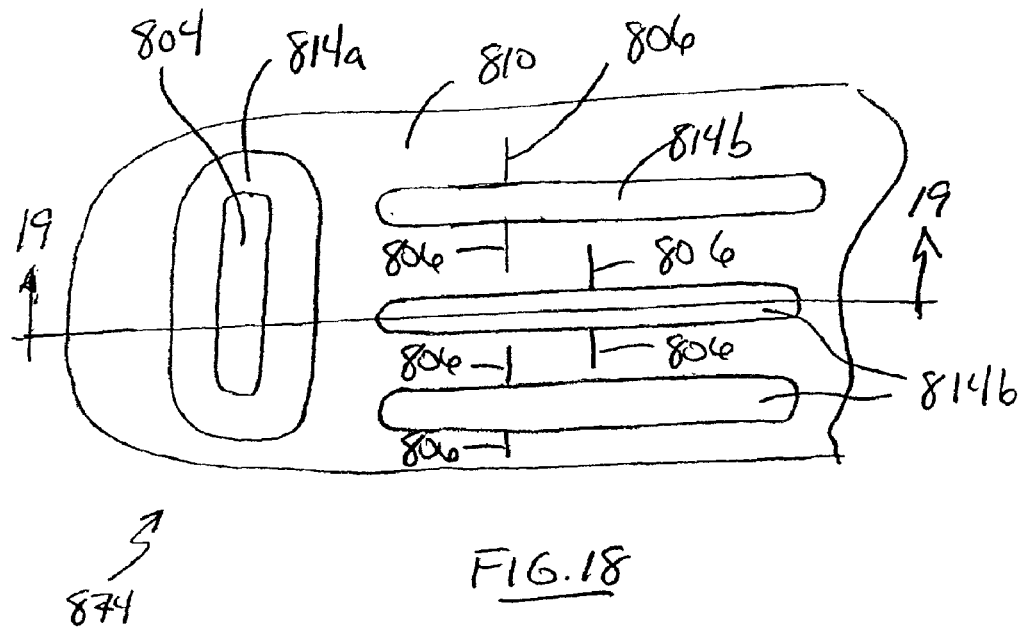
FIG. 18 is a plan view of one article manufactured from a composite web including elastomeric and nonelastomeric discrete polymeric regions.
Figure 19:
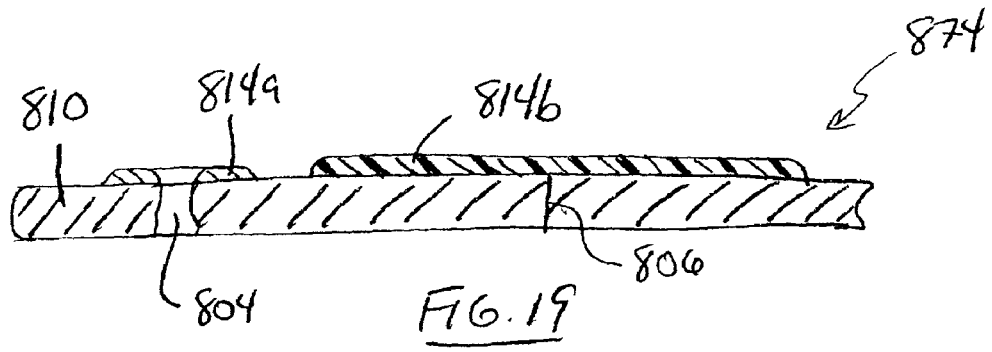
FIG. 19 is a cross-sectional view of the article of FIG. 18, taken along line 19—19 in FIG. 18.

One such example of an article that includes discrete polymeric regions that are either elastomeric or nonelastomeric is depicted in FIGS. 18 & 19. The article 874 may, for example, be provided as a fastening article that may be used in securing a garment (e.g., a diaper, gown, etc.) on a wearer. The article 874 includes a reinforcing ring 814*a* in the form of a discrete polymeric region formed of a nonelastomeric thermoplastic composition. Although only one discrete polymeric region 814*a* formed of a nonelastomeric thermoplastic composition is depicted in connection with the article 874, it will be understood that articles of the present invention may include one or more such reinforcing discrete polymeric regions.

The article 874 also includes elastomeric thermoplastic compositions in discrete polymeric regions 814*b*. Although three such regions are depicted in FIG. 18, it will be understood that articles of the present invention may include only one or more than one discrete polymeric regions formed of elastomeric thermoplastic compositions.

As seen in FIG. 19, a cross-sectional view of the article 874 of FIG. 18 taken along line 19—19 in FIG. 18, the different discrete polymeric regions 814*a* and 814*b* are provided on the same major surface of the substrate 810 on which the article 874 is formed. As discussed above, however, it will be understood that any combination of the discrete polymeric regions 814*a* and 814*b* may be located on the same or different major surfaces of the substrate 810.

Also depicted in FIG. 19 is an opening 804 formed through the substrate 810 within the surrounding ring of nonelastomeric thermoplastic composition forming the discrete polymeric region 814*a*. As discussed above in connection with FIG. 10, such openings may be formed by any suitable technique. This opening may, for example, be sized to receive a tab or other structure that fits within the slot formed by the opening 804 formed within the discrete polymeric region 814*a* in such a manner that retains the tab or other structure within the slot.

The fastening article 874 also includes discrete polymeric regions 814*b* that preferably function as elastic elements to provide elasticity to the article 874 if the substrate 810 is nonelastic. If the substrate 810 is itself elastic, the discrete polymeric regions 814*b* may still function as elastic elements that enhance the elasticity of the article 874.

Although the substrate 810 is preferably extensible, a nonextensible substrate 810 can be made extensible by, e.g., providing slits 806 in the substrate 810. The slits 806 are preferably spanned by at least one of the discrete elastomeric polymeric regions 814*b*. Some exemplary slitting processes to provide or improve extensibility of a substrate are described in International Publication No. WO 96/10481 (Abuto et al.). Other techniques may also be used to provide or improve the extensibility of substrates used in connection with the present invention. For example, the mechanical stretching processes described in U.S. Pat. Nos. 4,223,059 (Schwarz) and U.S. Pat. No. 5,167,897 (Weber et al.) may be used to provide or improve extensibility.

Figure 20:
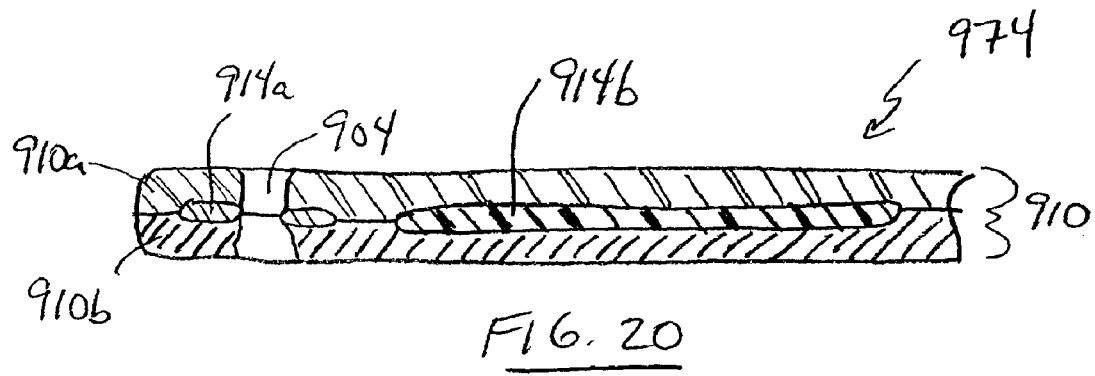
FIG. 20 is a cross-sectional view of an article manufactured from a laminated composite web including elastomeric and nonelastomeric discrete polymeric regions.

FIG. 20 depicts a laminated variation of the elastic fastening article 874 of FIGS. 18 and 19. The fastening article 974 includes two substrates 910*a* and 910*b* that are laminated together, such that the discrete polymeric regions 914*a* and 914*b* are located within the composite web 910. The article also includes an opening 904 formed within the reinforcing ring formed by the nonelastomeric thermoplastic composition of the discrete polymeric region 914*a*.

Figure 21:
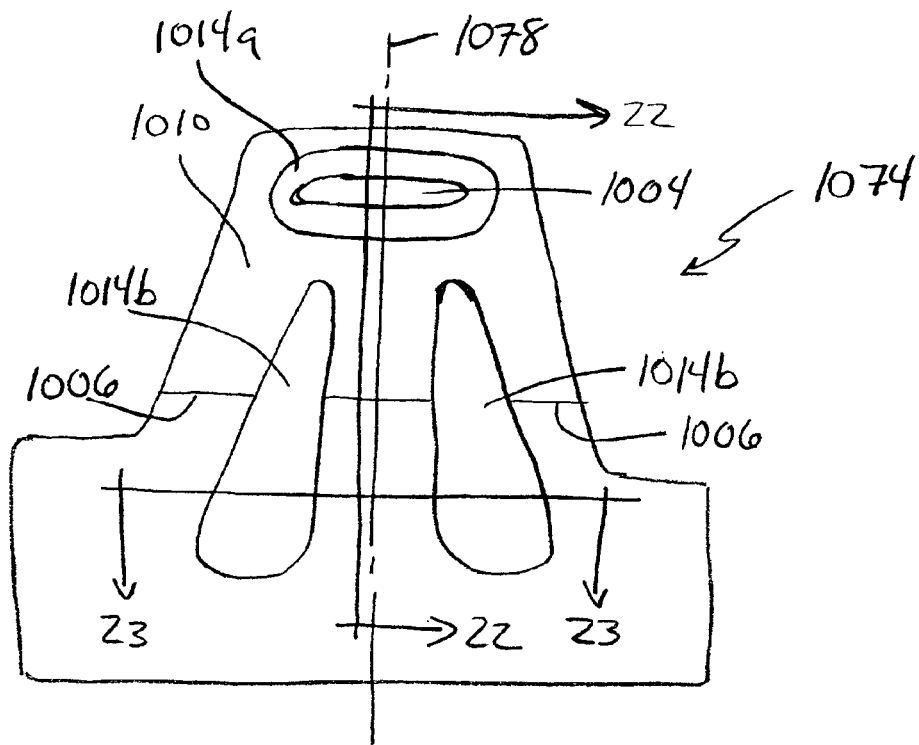
FIG. 21 is a plan view of another article manufactured from a composite web including elastomeric and nonelastomeric discrete polymeric regions.
Figure 22:
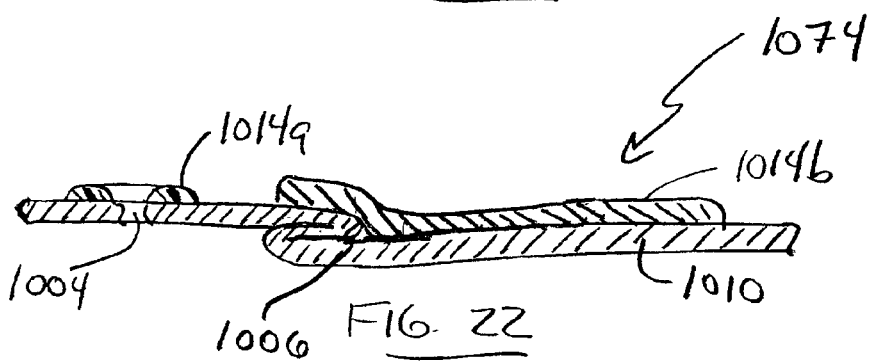
FIG. 22 is a cross-sectional view of the article of FIG. 21, taken along line 22—22 in FIG. 21.
Figure 23:
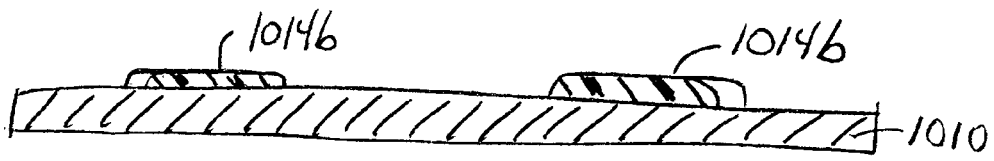
FIG. 23 is a cross-sectional view of the article of FIG. 21, taken along line 23—23 in FIG. 21.

FIGS. 21–23 depict various views of another fastening article according to the present invention. Fastening tab 1074 includes a substrate 1010 on which a variety of different discrete polymeric regions are located. The different discrete polymeric regions provide a reinforcing surrounding ring (1014*a*) for attaching the article 1074 to a complementary structure and elastic elements (1014*b*) to provide elasticity to the fastening article 1074. The tab 1074 preferably includes an elongation axis 1078 seen in FIG. 21.

Discrete polymeric region 1014*a* is provided proximate the distal end of the fastening article 1074. FIG. 22 is a cross-sectional view taken along line 22—22 in FIG. 21 and depicts a pleat 1006 formed in the substrate 1010, with the elastic elements 1014*b* spanning the pleat 1006. In the embodiment depicted in FIG. 22, the substrate 1010 includes only one pleat, although it should be understood that the articles of the present invention may include one or more pleats as desired for extensibility purposes.

The discrete polymeric region 1014*a* is formed of non-elastomeric materials and, as such, the discrete polymeric region 1014*a* may also function to distribute stresses over the width of the article 1074 (where the width is measured generally transverse to the elongation axis 1078 depicted in FIG. 21). It may be desirable to distribute the forces applied during elongation of the article 1074 to reduce or prevent necking or roping of the article 1074. Force distribution may also be helpful to improve uniformity in the forces seen across the width of the article 1074.

In the depicted embodiment, the elastomeric discrete polymeric regions 1014*b* are located on the same surface of the substrate 1010 as the nonelastomeric discrete polymeric region 1014*a*. Each of the elastomeric discrete polymeric regions 1014*b* preferably includes a length that is substantially aligned with the elongation axis 1078. For the purposes of the present invention, the length of the discrete polymeric regions 1014*b* is the longest straight line dimension of the discrete polymeric regions 1014*b* as measured along the surface of the substrate 1010.

Another feature of the elastomeric discrete polymeric regions 1014*b* is their nonuniform or changing width. As seen in FIG. 21, the discrete polymeric regions 1014*b* become wider when moving away from the discrete polymeric region 1014*a*. If the height or thickness of the discrete polymeric regions 1014*b* above the surface of the substrate 1010 is constant, the net result of the changing width depicted in FIG. 21 is that the amount of elastomeric material in the discrete polymeric regions 1014*b* increases when moving away from the discrete polymeric region 1014*a*. The changing bulk of elastomeric material may, e.g., provide an article 1074 that has different elasticity and/or elongation properties at different locations along the elongation axis 1078. Many other variations in the distribution of elastomeric material in the discrete polymeric regions 1014*b* may be used to tailor the elasticity and/or elongation properties of the fastening tab 1074, e.g., adjusting the thickness of the polymeric regions, the materials used, etc.

Figure 24:
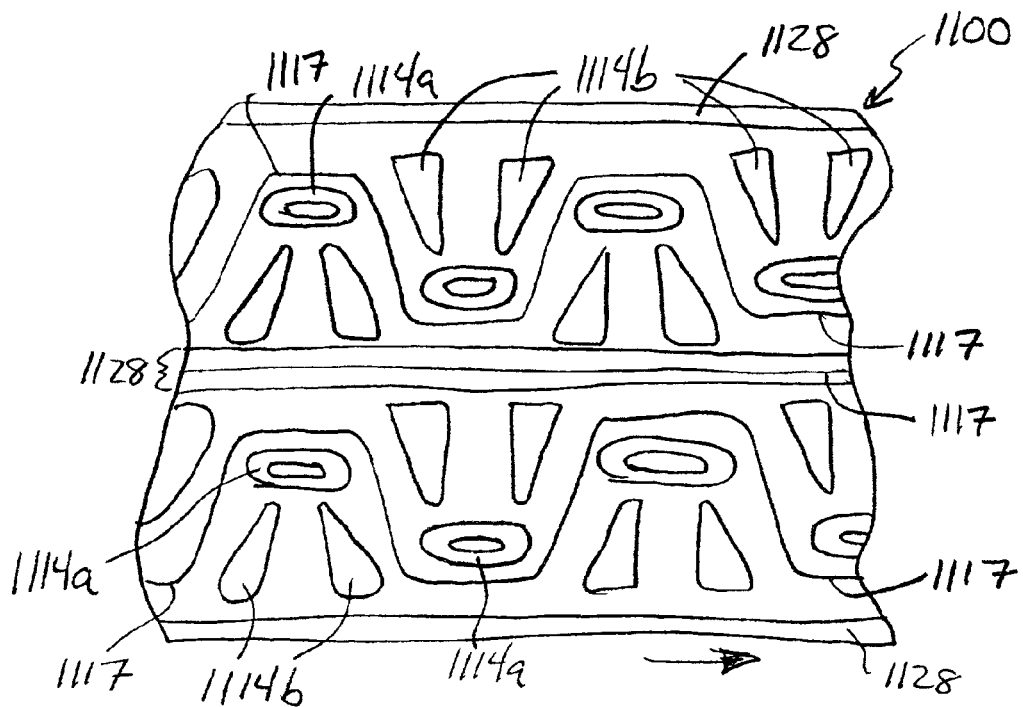
FIG. 24 is a plan view of one composite web according to the present invention, the composite web including lines of separation formed therein.

FIG. 24 depicts one composite web 1100 that may be, at least in part, manufactured using the system of FIG. 24. The composite web 1100 includes a variety of different discrete polymeric regions 1114*a* and 1114*b* located thereon. In addition, the composite web 1100 includes lines of separation 1117 that define the boundaries of a number of different fastening tabs similar to those described above with respect to FIGS. 21–23. The lines of separation 1117 define a nested configuration of fastening articles including the nonelastomeric discrete polymeric regions 1114*a* and elastomeric discrete polymeric regions 1114*b* in a manner that may reduce waste when the composite web 1100 is separated along the lines of separation 1117 to provide the desired fastening articles. The lines of separation 1117 may take on any suitable form that facilitates separation of the composite web 1100 along the lines of separation, e.g., score lines, lines of weakness, lines of perforations, etc.

The composite web 1100 preferably has a length that extends along the direction of the straight line of separation 1117 extending from left to right in FIG. 24. Although the composite web 1100 includes only two pairs of nested tabs across the width of the composite web 1100 (where width is transverse to length), it will be understood that any desired number of nested pairs of tabs may be provided in a single composite web according to the present invention.

Another optional feature depicted in FIG. 24 are bonding sites 1128 that, in the depicted embodiment, is provided in the form of strips extending along the central line of separation bisecting the composite web 1100, and along the edges of the composite web 1100. Although depicted as continuous strips that extend along the length of the composite web 1100, each of the elastic articles defined by the lines of separation 1117 may alternatively include one or more discrete bonding sites if so desired.

The bonding sites 1128 may be provided to assist in the attachment of the elastic articles defined by the lines of separation 1117 to a larger article, e.g., a diaper, gown, etc. To assist in attachment, the bonding sites 1128 may take a variety of configurations. For example, the bonding site may be a consolidated area of a nonwoven or woven fabric amenable to thermal or other consolidation techniques. Alternatively, or in addition to consolidation, the bonding sites may include one or more materials that assist in bonding, e.g., block copolymers, ethylene vinyl acetates, tackified ethylene vinyl acetates, adhesives (pressure sensitive, curable, heat activated, etc.), amorphous polyolefins, etc. The specific selection of materials to locate in the bonding sites 1128 will depend on the type of bonding to be performed and the materials to be bonded.

One advantage of the bonding sites 1128 is that they can be formed of materials that are particularly amenable to the attachment technique to be used, e.g., heat sealing, ultrasonic welding, etc. Another advantage is that the bonding sites can be sized such that they are large enough to accomplish their function, but not so large that any materials used in the bonding sites are wasted. Depending on the composition of the materials to be provided at the bonding sites, they may be formed by the transfer methods described herein if a thermoplastic composition is to be used in the bonding sites 1128.

If the elastic articles defined by the lines of separation 1117 are to be used as, e.g., fastening articles, it may be preferred that the bonding sites 1128 be adapted to receive a mechanical fastener or fasteners that may be bonded to the tab separately. Alternatively, an adhesive (e.g., pressure sensitive, curable, heat activated, etc.) or cohesive material could be provided within the bonding sites 1128.

The deposition of discrete polymeric regions formed of elastomeric thermoplastic compositions on a substrate may be accomplished in much the same manner as used in connection with the deposition of discrete polymeric regions formed of nonelastomeric thermoplastic compositions discussed above. The different thermoplastic compositions may be transferred to the substrates using a zoned system as discussed in connection with FIG. 12, or the different thermoplastic compositions may by transferred to the substrates at different transfer stations.

Figure 25:
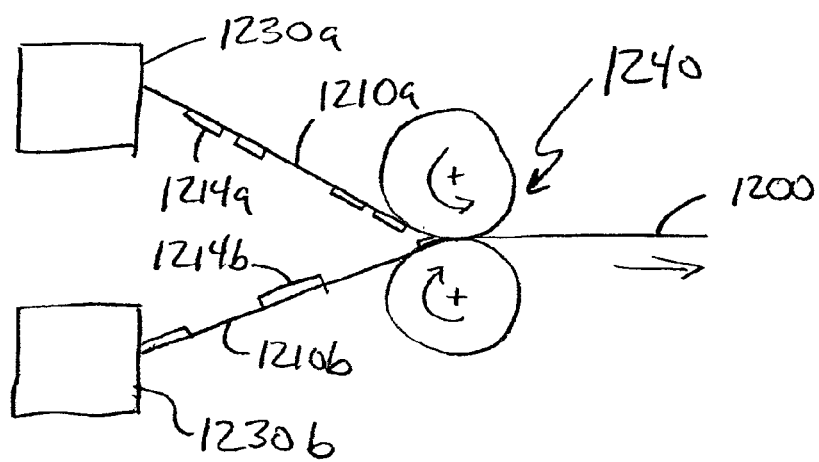
FIG. 25 is a schematic diagram of one system and method for manufacturing composite webs according to the present invention.

An alternative system may include lamination of two substrates together, with each substrate including one or the other of the elastomeric or nonelastomeric discrete polymeric regions as described, e.g., above. FIG. 25 is a schematic depiction of one such system and method in which a transfer station 1230*a* produces nonelastomeric discrete polymeric regions 1214*a* on substrate 1210*a*. Transfer station 1230*b* produces elastomeric discrete polymeric regions 1214*b* on substrate 1210*b*. Each of the transfer stations may, e.g., be constructed similar to the system depicted in FIG. 11.

Both substrates 1210*a* and 1210*b* are directed into a laminating station 1240 that produces a laminated composite web 1200 which, in the depicted embodiment, would provide both the nonelastomeric discrete polymeric regions 1214*a* and the elastomeric discrete polymeric regions 1214*b* located within the surrounding layers of substrates 1210*a* and 1210*b*. Alternatively, it will be understood that one or both sets of discrete polymeric regions could be laminated to the exterior of the laminated composite web 1200.

Figure 26:
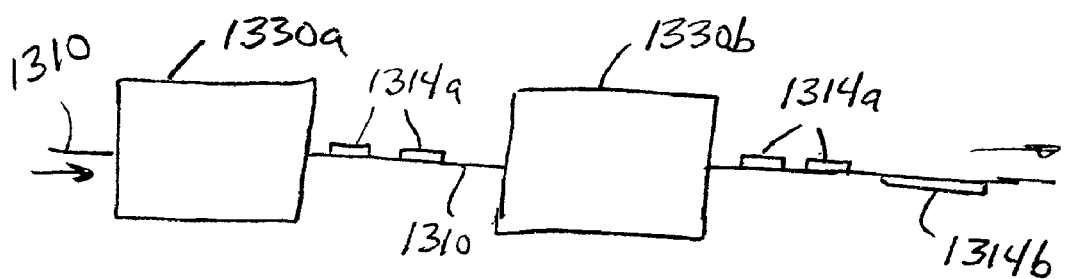
FIG. 26 is a schematic diagram of another system and method for manufacturing composite webs according to the present invention.

FIG. 26 depicts another system and method in which the different discrete polymeric regions 1314*a* and 1314*b* are sequentially deposited on the same substrate 1310. The system and method includes a transfer station 1330*a* in which the substrate 1310 is processed to provide a first set of discrete polymeric regions 1314*a* thereon. The substrate 1310 with discrete polymeric regions 1314*a* is then directed into a second transfer station 1330*b* in which a second set of discrete polymeric regions 1314*b* is provided on the substrate 1310. Although the second set of discrete polymeric regions 1314*b* are depicted as being located on the opposite side of the substrate 1310 from the first set of discrete polymeric regions 1314*a*, it will be understood that both sets of discrete polymeric regions could be located on the same side of the substrate 1310. In yet another alternative, the different sets of discrete polymeric regions could both be located on both sides of the substrate 1310.

The order in which any elastomeric and nonelastomeric discrete polymeric regions are deposited on the substrate 1310 may vary. Further, it will be understood that additional transfer stations could be added to the system and method depicted in FIG. 26 to provide more of the same discrete polymeric regions or yet additional different discrete polymeric regions on the substrate 1310. Further, additional stations may be added to laminate one or more additional substrates to the substrate 1310.

As with the nonelastomeric thermoplastic compositions described above, elastomeric thermoplastic compositions used for elastic discrete polymeric regions should be capable of flowing or entering into depressions formed in a polymer transfer roll as will be described below. Suitable elastomeric thermoplastic compositions are those that are melt processable. Such polymers are those that will flow sufficiently to at least partially fill the depressions, yet not significantly degrade during a melt process. A wide variety of elastomeric thermoplastic compositions have suitable melt and flow characteristics for use in the process of the present invention depending on the geometry of the depressions and the processing conditions. It may further be preferred that the melt processable materials and conditions of processing are selected such that any viscoelastic recovery properties of the thermoplastic composition do not cause it to significantly withdraw from the wall(s) of the depressions until transfer of the thermoplastic composition to a substrate is desired.

As used in connection with the present invention, "elastomeric" means that the material will substantially resume its original shape after being stretched. Further, the elastomeric materials may preferably sustain only small permanent set following deformation and relaxation, which set is preferably no greater than about 30 percent and more preferably no greater than about 20 percent of the original length at moderate elongation, e.g., about 50%. The elastomeric materials can be both pure elastomers and blends with an elastomeric phase or content that will still exhibit substantial elastomeric properties at room temperature. U.S. Pat. No. 5,501,679 (Krueger et al.) provides some further discussion regarding elastomeric materials that may be considered for use in connection with the present invention.

The elastomeric thermoplastic compositions can include one or more polymers. For example, the elastomeric thermoplastic composition could be a blend with an elastomeric phase such that the composition exhibits elastomeric properties at room temperature. Suitable elastic thermoplastic polymers include block copolymers such as conventional A-B or A-B-A block copolymers (e.g., styrene-isoprene-styrene, styrene-butadiene-styrene, styrene-ethylene-butylene-styrene block copolymers), elastomeric polyurethanes, olefinic elastomers, particularly elastomeric ethylene copolymers (e.g., ethylene vinyl acetates, ethylene/octene copolymer elastomers, ethylene/propylene/diene terpolymer elastomers), as well as mixtures of these with each other, with other elastomeric thermoplastic polymers, or with nonelastomeric thermoplastic polymers.

The elastomeric thermoplastic compositions used in connection with the present invention can also be combined with various additives for desired effect. These include, for example, fillers, viscosity reducing agents, plasticizers, tackifiers, colorants (e.g., dyes or pigments), antioxidants, antistatic agents, bonding aids, antiblocking agents, slip agents, stabilizers (e.g., thermal and ultraviolet), foaming agents, microspheres, glass bubbles, reinforcing fibers (e.g., microfibers), internal release agents, thermally conductive particles, electrically conductive particles, and the like. The amounts of such materials that can be useful in the thermoplastic compositions can be readily determined by those skilled in the art of processing and using such materials.

In addition to the deposition of nonelastic or elastic thermoplastic polymer in discrete regions, it is also contemplated that additional materials can be coated onto a major surface of the substrate using known methods. Such materials could be, for example adhesives, as described in, e.g., U.S. Pat. No. 5,019,071 (Bany et al.); U.S. Pat. No. 5,028,646 (Miller et al.); and U.S. Pat. No. 5,300,057 (Miller et al.); or cohesives as described in, e.g. U.S. Pat. No. 5,389,438 (Miller et al.) and U.S. Pat. No. 6,261,278 (Chen et al.).

EXAMPLE

The following example is provided to enhance understanding of the present invention. The example is not intended to limit the scope of the invention.

To demonstrate that two different polymers can be used to produce both an elastic region and a reinforcing region on two different substrates followed by lamination, a web was prepared using the apparatus shown in FIG. 11, except a second transfer roll, similar to the transfer roll 30, a second rubber backup roll, similar to the rubber backup roll 20, a second doctor blade, similar to the doctor blade 42, and a second hot wire, similar to the hot wire 44, were used to transfer a discrete reinforcing polymer region to a second nonwoven substrate (SONTARA 8001 spunlaced polyester, Dupont). KRATON G-1657 SEBS block copolymer was used as the molten polymer for delivery to transfer roll 30 at a melt temperature of 246° C. using a 40 mm twin screw extruder. SONTARA 8001 spunlaced polyester (Dupont) was used as the substrate 10.

Transfer roll 30 was machined with seven different areas arranged around and across the periphery of the roll, each area having a specific depression geometry and spacing. Area 1 was machined using a computer controlled milling machine (2 mm ball diameter) to have depressions in the shape of grooves parallel to the roll axis 25 mm long, 0.75 mm in depth, 13 mm end to end spacing measured along the roll axis, 7.5 mm center to center spacing between grooves measured normal to the roll axis, with 12 rows of staggered grooves. Each row of grooves starting with a 6.4 mm shift from the previous row to create the staggered pattern. Area 2 was machined using a computer controlled milling machine (2 mm ball diameter) to have 15 rows of grooves parallel to the roll axis 114 mm long, 0.375 mm in depth, and 6.0 mm center to center spacing between grooves measured normal to the roll axis. Area 3 was machined using a computer controlled milling machine (2 mm ball diameter) to have 15 rows of grooves parallel to the roll axis 114 mm long, 0.5 mm in depth, and 6.0 mm center to center spacing between grooves measured normal to the roll axis. Area 4 was machined using a computer controlled milling machine (2 mm ball diameter) to have 12 rows of grooves parallel to the roll axis 114 mm long, 0.5 mm in depth, and 7.5 mm center to center spacing between grooves measured normal to the roll axis. Area 5 was machined using a computer controlled milling machine (2 mm ball diameter) to have 12 rows of grooves parallel to the roll axis 114 mm long, 0.875 mm in depth, and 7.5 mm center to center spacing between grooves measured normal to the roll axis. Area 6 was machined using a computer controlled milling machine (2 mm ball diameter) to have 9 rows of grooves parallel to the roll axis 114 mm long, 1.0 mm in depth, and 10.0 mm center to center spacing between grooves measured normal to the roll axis. Area 7 was machined using a computer controlled milling machine (3 mm ball diameter) to have 9 rows of grooves parallel to the roll axis 114 mm long, 0.75 mm in depth, and 10.0 mm center to center spacing between grooves measured normal to the roll axis.

The temperature of the second transfer roll was 232° C. The brass doctor blade 42 having a thickness of 1.5 mm at the point of contact with the transfer roll 30, was pressed firmly against and normal to the exterior surface of the transfer roll at a pressure of 123 N/lineal cm. A nip pressure of 12 N/lineal cm between the transfer roll and rubber backup roll (20° C.) was used. SC-917 polypropylene (Basell Olefins) was used as the molten polymer for delivery to the second transfer roll at a melt temperature of 227° C. using a 19 mm single screw extruder.

The second transfer roll was machined using a computer controlled milling machine to have a circle of 8 depressions around the periphery of the roll near the center of the roll positioned so as not to overlap the depressions in transfer roll 30 forming the elastic regions. The depressions were elliptical in shape 7.6 cm long and 1.9 cm in width at the widest point of the ellipse. The long axis of each ellipse was parallel to the machine direction (downweb). The ellipses were arranged with a center-to-center spacing of 8.9 cm. The elliptical depressions were machined in a seven step process. Step 1 consisted of milling 0.333 mm depth cells using a 2 mm tool in a 7.6 cm by 1.9 cm elliptical pattern. Step 2 consisted of milling 0.500 mm depth cells using a 3 mm tool. Step 3 consisted of milling 0.666 mm depth cells using a 4 mm tool. Step 4 consisted of milling 0.833 mm depth cells using a 5 mm tool. Step 5 consisted of milling 0.999 mm depth cells using a 6 mm tool. Step 6 consisted of milling 1.165 mm depth cells using a 7 mm tool. Step 7 consisted of milling 1.332 mm depth cells using a 8 mm tool. The cells were positioned such that the deeper cells were in the middle of the ellipse with progressively shallower cells tapering outwards towards the perimeter of the ellipse.

The temperature of the transfer roll was 227° C. The pressure of the doctor blade against the second transfer roll was 123 N/lineal cm. A nip pressure of 25 N/lineal cm between the transfer roll and rubber backup roll (20° C.) was used. SONTARA 8001 spunlaced polyester (Dupont) was used as the substrate. A nip pressure of 6 N/lineal cm between the two rubber rolls was used to laminate the two substrates together resulting in a web that had discrete elastic polymeric regions and discrete reinforcing polymer regions.

The preceding specific embodiments are illustrative of the practice of the invention. This invention may be suitably practiced in the absence of any element or item not specifically described in this document. The complete disclosures of all patents, patent applications, and publications are incorporated into this document by reference as if individually incorporated. Various modifications and alterations of this invention will become apparent to those skilled in the art without departing from the scope of this invention. It should be understood that this invention is not to be unduly limited to illustrative embodiments set forth herein.

What is claimed is:

1. An elastic article comprising: a substrate comprising first and second major surfaces;

one or more reinforcing discrete polymeric regions attached to the substrate, wherein each reinforcing discrete polymeric region of the one or more reinforcing discrete polymeric regions comprises a nonelastomeric thermoplastic composition that infiltrates a portion of substrate; and one or more elastic elements attached to the substrate, wherein each elastic element of the one or more elastic elements comprises an elastic discrete polymeric region comprising an elastomeric thermoplastic composition that infiltrates a portion of the substrate.

2. An article according to claim 1, wherein the substrate comprises a laminated substrate comprising a first substrate and a second substrate, wherein each elastic element of the one or more elastic elements is located between the first substrate and the second substrate.

3. An article according to claim 1, wherein at least one elastic element of the one or more elastic elements is located on the first major surface of the substrate.

4. An article according to claim 1, wherein at least one elastic element of the one or more elastic elements is located on the second major surface of the substrate.

5. An article according to claim 1, further comprising an elongation axis, wherein each elastic element of the one or more elastic elements comprises a length greater than a width, and wherein the length of each elastic element of the one or more elastic elements is aligned with the elongation axis.

6. An article according to claim 5, wherein the amount of elastomeric thermoplastic in each elastic element of the one or more elastic elements increases when moving away from the one or more reinforcing discrete polymeric regions along the elongation axis.

7. An article according to claim 1, wherein at least one reinforcing discrete polymeric region of the one or more reinforcing discrete polymeric regions comprises an opening formed through the substrate within a surrounding ring formed of the nonelastomeric thermoplastic composition of the at least one reinforcing discrete polymeric region.

8. An article according to claim 1, further comprising one or more slits formed through the substrate, wherein at least one of the one or more elastic elements spans at least one slit of the one or more slits.

9. An article according to claim 1, further comprising one or more pleats formed in the substrate, wherein at least one of the one or more elastic elements spans at least one pleat of the one or more pleats.

10. An article according to claim 9, wherein at least some elastic elements of the one or more elastic elements spans only one pleat of the one or more pleats.

11. An article according to claim 9, at least some elastic elements of the one or more elastic elements span two or more pleats of the one or more pleats.

12. A composite web comprising:

a substrate comprising first and second major surfaces;

a plurality of nonelastomeric discrete polymeric regions attached to the substrate, wherein each nonelastomeric discrete polymeric region of the plurality of nonelastomeric discrete polymeric regions comprises a nonelastomeric thermoplastic composition that infiltrates a portion of substrate;

a plurality of elastomeric discrete polymeric regions attached to the substrate, wherein each elastomeric discrete polymeric region of the plurality of elastomeric discrete polymeric regions comprises an elastomeric thermoplastic composition that infiltrates a portion of the substrate; and one or more lines of separation in the composite web, wherein the one or more lines of separation define boundaries of a plurality of distinct articles in the composite web, and wherein each article of the plurality of articles comprising at least one nonelastomeric discrete polymeric region of the plurality of nonelastomeric discrete polymeric regions and at least one elastomeric discrete polymeric region of the plurality of elastomeric discrete polymeric regions.

13. A composite web according to claim 12, wherein the substrate comprises a laminated substrate comprising a first substrate and a second substrate, wherein each elastomeric discrete polymeric region of the plurality of elastomeric discrete polymeric regions is located between the first substrate and the second substrate.

14. A composite web according to claim 12, wherein the substrate comprises a laminated substrate comprising a first substrate and a second substrate, wherein each elastomeric discrete polymeric region of the plurality of elastomeric discrete polymeric regions is located on the first major surface or the second major surface of the substrate.

15. A composite web according to claim 12, wherein the substrate comprises a laminated substrate comprising a first substrate and a second substrate, wherein each nonelastomeric discrete polymeric region of the plurality of nonelastomeric discrete polymeric regions is located between the first substrate and the second substrate.

16. A composite web according to claim 12, wherein the substrate comprises a laminated substrate comprising a first substrate and a second substrate, wherein each nonelastomeric discrete polymeric region of the plurality of nonelastomeric discrete polymeric regions is located on the first major surface or the second major surface of the substrate.

* * * * *

UNITED STATES PATENT AND TRADEMARK OFFICE
CERTIFICATE OF CORRECTION

PATENT NO. : 6,875,710 B2
DATED : April 5, 2005
INVENTOR(S) : Eaton, Bradley W.

It is certified that error appears in the above-identified patent and that said Letters Patent is hereby corrected as shown below:

Title page,
Item [56], References Cited, U.S. PATENT DOCUMENTS, please add:

| | | |
|---|---|---|
| -- 2,170,560 | 8/1939 | Hayes |
| 2,787,244 | 4/1957 | Hicken |
| 3,276,944 | 10/1966 | Levy |
| 3,338,992 | 8/1967 | Kinney |
| 3,341,394 | 9/1967 | Kinney |
| 3,502,538 | 3/1970 | Peterson |
| 3,502,763 | 3/1970 | Hartman |
| 3,542,614 | 11/1970 | Dobo et al. |
| 3,692,618 | 9/1972 | Dorschner et al. |
| 3,694,867 | 10/1972 | Stumpf |
| 3,814,052 | 6/1974 | Caratsch |
| 4,223,059 | 9/1980 | Schwarz |
| 4,340,563 | 7/1982 | Appel et al. |
| 4,343,260 | 8/1982 | Yajima et al. |
| 4,643,130 | 2/1987 | Sheath et al. |
| 4,732,800 | 3/1988 | Groshens |
| 4,906,492 | 3/1990 | Groshens |
| 4,965,122 | 10/1990 | Morman |
| 4,981,747 | 1/1991 | Morman |
| 4,984,339 | 1/1991 | Provost et al. |
| 5,019,071 | 5/1991 | Bany et al. |
| 5,028,646 | 7/1991 | Miller et al. |
| 5,077,870 | 1/1992 | Melbye et al. |
| 5,114,781 | 5/1992 | Morman |
| 5,116,563 | 5/1992 | Thomas et al. |
| 5,116,662 | 5/1992 | Morman |
| 5,167,897 | 12/1992 | Weber |
| 5,226,992 | 7/1993 | Morman |
| 5,260,015 | 11/1993 | Kennedy et al. |
| 5,300,057 | 4/1994 | Miller et al. |
| 5,326,415 | 7/1994 | Thomas et al. |
| 5,385,706 | 1/1995 | Thomas |
| 5,389,438 | 2/1995 | Miller et al. |
| 5,399,219 | 3/1995 | Roessler et al. |
| 5,441,687 | 8/1995 | Murasaki et al. |
| 5,454,801 | 10/1995 | Lauritzen |
| 5,470,424 | 11/1995 | Isaac et al. |
| 5,490,457 | 2/1996 | Boulanger et al. |
| 5,501,679 | 3/1996 | Krueger et al. |

UNITED STATES PATENT AND TRADEMARK OFFICE
CERTIFICATE OF CORRECTION

PATENT NO. : 6,875,710 B2  
DATED : April 5, 2005  
INVENTOR(S) : Eaton, Bradley W.

Page 2 of 3

It is certified that error appears in the above-identified patent and that said Letters Patent is hereby corrected as shown below:

Title page, (cont'd),

| | | |
|---|---|---|
| 5,578,344 | 11/1996 | Ahr et al. |
| 5,679,302 | 10/1997 | Miller et al. |
| 5,685,758 | 11/1997 | Paul et al. |
| 5,685,873 | 11/1997 | Bruemmer |
| 5,705,013 | 1/1998 | Nease et al. |
| 5,755,015 | 5/1998 | Akeno et al. |
| 5,792,411 | 8/1998 | Morris et al. |
| 5,827,579 | 10/1998 | Groshens |
| 5,868,987 | 2/1999 | Kampfer et al. |
| 5,916,207 | 6/1999 | Toyoda |
| 5,948,707 | 9/1999 | Crawley |
| 6,039,911 | 3/2000 | Miller et al. |
| 6,054,091 | 4/2000 | Miller et al. |
| 6,093,665 | 7/2000 | Sayovitz et al. |
| 6,132,411 | 10/2000 | Huber et al. |
| 6,132,660 | 10/2000 | Kampfer |
| 6,190,594 B1 | 2/2001 | Gorman et al. |
| 6,255,236 B1 | 7/2001 | Cree et al. |
| 6,261,278 B1 | 7/2001 | Chen et al. |
| 6,287,665 B1 | 9/2001 | Hammer --. |

UNITED STATES PATENT AND TRADEMARK OFFICE
CERTIFICATE OF CORRECTION

PATENT NO. : 6,875,710 B2
DATED : April 5, 2005
INVENTOR(S) : Eaton, Bradley W.

It is certified that error appears in the above-identified patent and that said Letters Patent is hereby corrected as shown below:

<u>Title page, (cont'd),</u>
FOREIGN PATENT DOCUMENTS, please add:
-- FR                 2184741             12/1973
   WO           WO 96/10481 A1    4/1996
   WO           WO 00/20200 A1    4/2000
   WO           WO 00/50229 A1    8/2000
   WO           WO 01/68019 A1    9/2001
   WO           WO 01/71080 A1    9/2001 --.

Signed and Sealed this

Sixth Day of December, 2005

JON W. DUDAS
*Director of the United States Patent and Trademark Office*